(12) United States Patent
Ji et al.

(10) Patent No.: US 8,658,778 B2
(45) Date of Patent: Feb. 25, 2014

(54) HTMC PROMOTER AND VECTORS FOR THE TUMOR-SELECTIVE AND HIGH-EFFICIENT EXPRESSION OF CANCER THERAPEUTIC GENES

(75) Inventors: Lin X. Ji, Sugar Land, TX (US); Bingliang Fang, Pearland, TX (US); Jack A. Roth, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1402 days.

(21) Appl. No.: 11/372,246

(22) Filed: Mar. 9, 2006

(65) Prior Publication Data

US 2007/0092968 A1 Apr. 26, 2007

Related U.S. Application Data

(60) Provisional application No. 60/659,935, filed on Mar. 9, 2005.

(51) Int. Cl.
*C07H 21/04* (2006.01)

(52) U.S. Cl.
USPC .......................................... 536/24.1; 536/23.5

(58) Field of Classification Search
None
See application file for complete search history.

(56) References Cited

U.S. PATENT DOCUMENTS

| | | | |
|---|---|---|---|
| 5,753,627 A | 5/1998 | Albert et al. | 514/16 |
| 6,017,509 A | 1/2000 | Dean et al. | 424/1.69 |
| 6,054,575 A | 4/2000 | Villeponteau et al. | 536/24.31 |
| 6,610,839 B1 | 8/2003 | Morin et al. | 536/24.1 |
| 6,617,110 B1 | 9/2003 | Cech et al. | 435/6 |
| 6,713,055 B2 | 3/2004 | Schiff | 424/93.21 |
| 2001/0029035 A1 | 10/2001 | Eisenhut et al. | 435/69.4 |
| 2002/0164715 A1 | 11/2002 | Ji et al. | 435/69.5 |
| 2002/0173626 A1 | 11/2002 | Kundra | 530/350 |
| 2003/0082722 A1 | 5/2003 | Fang | 435/69.1 |
| 2003/0099616 A1 | 5/2003 | Irving et al. | 424/93.2 |
| 2003/0110519 A1 | 6/2003 | Goodearl et al. | 800/8 |
| 2003/0166061 A1 | 9/2003 | Glucksmann et al. | 435/69.1 |
| 2004/0102364 A1 | 5/2004 | Bonasera et al. | 514/9 |
| 2004/0173626 A1 | 9/2004 | Jeor | 220/745 |
| 2007/0173545 A1* | 7/2007 | Verma et al. | 514/506 |

FOREIGN PATENT DOCUMENTS

| | | | |
|---|---|---|---|
| AU | 763956 | 8/2001 | |
| EP | 0508221 | 10/1992 | |
| WO | WO 96/39542 | * 12/1996 | ............... C12Q 1/70 |
| WO | WO 99/38964 | 8/1999 | |
| WO | WO 00/00611 | 1/2000 | |
| WO | WO 00/46355 | 8/2000 | |

OTHER PUBLICATIONS

Wang et al., Enhanced suicide gene therapy by chimeric tumor-specific promoter based on HSF1 transcriptional regulation. FEBS Lett. 546(2-3):315-20, 2003.*
Zinn et al., Gamma camera dual imaging with a somatostatin receptor and thymidine kinase after gene transfer with a bicistronic adenovirus in mice. Radiology, 223(2):417-25, 2002.*
Martinez-Salas, Internal ribosome entry site biology and its use in expression vectors. Curr Opin Biotechnol. 10(5):458-64, 1999.*
Takakura et al., Cloning of human telomerase catalytic subunit (hTERT) gene promoter and identification of proximal core promoter sequences essential for transcriptional activation in immortalized and cancer cells, Cancer Res. 59(3):551-7, 1999.*
Promega 1997 catalogue (pp. 422-424).*
Xia et al., High levels of protein expression using different mammalian CMV promoters in several cell lines, Protein Expr. Purif. 45(1):115-24, 2006.*
Champton et al., Effect of intron A from human cytomegalovirus (Towne) immediate-early gene on heterologous expression in mammalian cells, Nucleic Acids Res. 19(14):3979-86, 1991.*
Abdul-Ghani et al., "Use of Transcriptional Regulatory Sequences of Telomerase (hTER and hTERT) for Selective Killing of Cancer Cells," *Mol. Ther.*, 2: 539-544, 2000.
Anton et al., "Use of the norepinephrine transporter as a reporter gene for non-invasive imaging of genetically modified cells," *J. Gene Med.*, 6:119-126, 2004.
Artemov et al., "MR Molecular Imaging of the Her-2/new Receptor in Breast Cancer Cells Using Targeted Iron Oxide Nanoparticles," *Mag. Reson. Med.*, 49:403-408, 2003.
Beattie et al., "Reconstitution of human telomerase activity in vitro," *Curr. Biol.*, 8(3):177-180, 1998.
Blackburn et al., "Apolipoprotein A-I decreases neutrophil degranulation and superoxide production,"*J. Lipid. Res.*, 32(12):1911-1918, 1991.
Blasberg, "Molecular Imaging and Cancer," *Mol. Cancer Ther.*, 2:335-343, 2003.
Braunstein et al., "Human telomerase reverse transcriptase promoter regulation in normal and malignant human ovarian epithelial cells," *Cancer Research*, 61:5529-36, 2001.
Buchsbaum et al., "Gene Expression imaging with radiolabeled peptides," *Annals of Nuclear Med.*, 18:275-283, 2004.

(Continued)

*Primary Examiner* — Valarie Bertoglio
(74) *Attorney, Agent, or Firm* — Parker Highlander PLLC

(57) ABSTRACT

Promoters that include a tissue-selective promoter sequence and a second promoter sequence operatively coupled to the tissue-selective promoter sequence, wherein the second promoter sequence includes a minimal viral promoter sequence, are disclosed. Nucleic acids and compositions that include these promoter sequences are also disclosed. Also disclosed are methods of improving the function of a tissue-selective promoter, involving operatively coupling a tissue-selective promoter sequence with a second promoter sequence that includes a minimal viral promoter sequence. Also disclosed are methods of delivering a gene into a cell, methods of treating a subject with a hyperproliferative disease, and methods of imaging a cell that involve use of the novel promoter sequences set forth herein.

35 Claims, 10 Drawing Sheets

(56) References Cited

OTHER PUBLICATIONS

Buchsbaum et al., "Radiotargeted Gene Therapy," *J. Nucl. Med.*, 46:179S-186S, 2005.
Chan et al., "Role of prolyl hydroxylation in onconically stablixed hypoxia-inducible factor-1α," *J. Biol. Chem.*, 277:40112-40117, 2002.
Contag et al., "Use of reporter genes for optical measurements of neoplastic disease in vivo," *Neoplasis*, 2(1-2):41-52, 2000.
Edinger et al., "Noninvasive assessment of tumor cell proliferation in animal models," *Neoplasia*, 1(4):303-10, 1999.
Felder, "Muscarinic acetylcholine receptors: signal transduction through multiple effectors," *FASEB J.*, 9:619-625, 1995.
Feng et al., "The RNA Component of Human Telomerase," *Science*, 269(5228):1236-1241, 1995.
Groot-Wasrink et al., "Noninvasive imaging of the transcriptional activities of human telomerase promoter fragments in mice," *Cancer Research*, 64(14):4906-4911, 2004.
Gu et al., "A novel single tetracycline-regulative adenoviral vector for tumor-specific Bax gene expression and cell killing in vitro and in vivo," *Oncogene*, 21:4757-4764, 2002.
Gu et al., "hTERT promoter induces tumor-specific bax gene expression and cell killing in syngenic mouse tumor model and prevents systemic toxicity," *Gene Ther.*, 9:30-37, 2002.
Gupta and Curtis, "Surface modified superparamagnetic nanopaticles for drug delivery: Interaction studies with human fibroblasts in culture," *J. Mat. Sci. Mat. Med.*, 15:493-496, 2004.
Gutkind et al., "Muscarinic acetylcholine receptor subtypes as agonist-dependent oncogenes," *Proc. Natl. Acad. Sci. USA*, 88:4703-4707, 1991.
Harrington et al., "Human telomerase contains evolutionarily conserved catalytic and structural subunits," *Gene Dev.*, 11:3109-3115, 1997.
Hemminki et al., "An Adenovirus with Enhanced Infectivity Mediates Molecular Chemotherapy of Ovarian Cancer Cells and Allows Imaging of Gene Expression," *Molecular therapy*, 4(3):223-231, 2001.
Hemminki, "In Vivo Molecular Chemotherapy and Noninvasive Imaging With an Infectivity-Enhanced Adenovirus," *JNCI*, 94(10):741-749, 2002.
Irving et al., "Conditionally replicative adenovirus driven by the human telomerase promoter provides broad-spectrum antitumor activity without liver toxicity," *Cancer Gene Therapy*, 11:174-185, 2004.
Ito et al., "Liposomal vector mediated delivery of the 3p FUS1 gene demonstrates potent antitumor activity against human lung cancer in vivo," *Cancer Gene Therapy*, 11:733-739, 2004.
Iyer et al., "Two-step transcriptional amplification as a method for imaging reporter gene expression using weak promoters," *Proc. Natl. Acad. Sci. USA*, 98(25):14595-14600, 2001.
Ji et al., "Expression of several genes in the human chromosome 3p21.3 homozygous deletion region by an adenovirus vector results in tumor suppressor activities in vitro and in vivo," *Cancer Res.*, 62:2715-2720, 2002.
Kagawa et al., "Antitumor activity and bystander effects of the tumor necrosis factor-related apoptosis-inducing ligand (trail) gene," *Cancer Res.*, 61:3330-3338, 2001.
Kawashima et al., "Telomerase-Specific replication-selective virotherapy for human cancer," *Clinical Cancer Res.*, 10:285-292, 2004.
Kikuchi et al., "Clarithromycin suppresses lipopolysancharide-induced interleukin-8 production by human monocytes through AP-1 and NF-kappaB transcription factors," *J of Antimicrobial Chemotherapy*, 49:745-755, 2002.
Kim et al., "Crystal Structure of the Hepatitis C Virus NS3 Protease Domain Complexed with a Synthetic NS4A Cofactor Peptide," *Cell*, 87:343-355, 1996.
Koller et al., "A generic method for the production of cell lines expressing high levels of 7-transmembrane receptors," *Analy Biochem*, 250:51-60, 1997.
Komata et al., "Treatment of malignant glioma cells with the transfer of constitutively active caspase-6 using the human telomerase catalytic subunit (human telomerase reverse transcriptase) gene promoter," *Cancer Res.*, 61(15):5796-5802, 2001.
Krejci et al., "Multiple promoters drive tissue-specific expression of the human M muscarinic acetylcholine receptor gene," *J. Neurochem.*, 91:88-98, 2004.
Kundra et al., "Noninvasive Monitoring of Somatostatin Receptor Type 2 Chimeric Gene Transfer," *J. Nuclear Med.*, 43:406-412, 2002.
Liang et al., "Noninvasive, quantitative imaging in living animals of a mutant dopamine D2 receptor reporter gene in which ligand binding is uncoupled from signal transduction," *Gene Therapy*, 8:1490-1498, 2001.
MacDonald and Hansell, Staging of non-small cell lung cancer: imaging of intrathoracic disease, *Eur. J. Radiology*, 45:18-30, 2003.
MacLaren et al., "Repetitive, non-invasive imaging of the dopamine D2 receptor as a reporter gene in living animals," *Gene Ther.*, 6(5):785-91, 1999.
McGraw, "Transgenic techniques to delineate cell-specific effects of beta2-adrenergic receptors in the lung," *J. Allergy Clin. Immunol.*, 110:S236-241, 2002.
Meyerson et al., "hEST2, the Putative Human Telomerase Catalytic Subunit Gene, Is Up-Regulated in Tumor Cells and during Immortalization," *Cell*, 90:785-795, 1997.
Nakamura et al., "Telomerase Catalytic Subunit Homologs from Fission Yeast and Human," *Science*, 277:955-959, 1997.
Nakayama et al., "Telomerase activation by hTRT in human normal fibroblasts and hepatocellular carcinomas," *Nature Genet.*, 18:65-68, 1998.
Pitcher et al., "G protein-coupled receptor kinases," *Annu. Rev, Biochem.*, 67:653-92, 1998.
Rehemtulla et al., "Rapid and quantitative assessment of cancer treatment response using in vivo bioluminescence imaging," *Neoplasis*, 2(6):491-5, 2000.
Rein et al., "Evaluation of tissue-specific promoters in carcinomas of the cervix uteri," *J. Gene Med.*, 6:1281-1289, 2004.
Reynolds et al., "A targetable, injectable adenoviral vector for selective gene delivery to pulmonary endothelium in vivo," *Mol Ther.*, 2(6):562-78, 2000.
Rogers et al., Non-invasive gamma camera imaging of gene transfer using an adenoviral vector encoding an epitope-tagged receptor as a reporter, *Gene Therapy*, 10:105-114, 2003.
Roth et al., "Endocytosis of the rat somatostatin receptors: subtype discrimination, ligand specificity, and delineation of carboxyterminal positive and negative sequence motifs," *DNA Cell Biol.*, 16:111-9, 1997.
Roth et al., "Phosphorylation of four amino acid residues in the carboxyl terminus of the rat somatostatin receptor subtype 3 is crucial for its desensitization and internalization," *J. Biol. Chem*, 272:23769-23774, 1997.
Shapiro et al., "Isolation, Sequence, and Functional Expression of the Mouse M1 Muscarinic Acetylcholine Receptor Gene," *J. Biol. Chem.*, 263:18397-18403, 1988.
Shay et al., "Telomeres and telomerase in human leukemias," *Leukemia*, 10(8):1255-1261, 1996.
Shi et al., "Antisense imaging of gene expression in the brain in vivo," *Proc Natl Acad Sci USA.*, 97(26):14709-14, 2000.
Stackhouse et al., "Specific membrane receptor gene expression targeted with radiolabeled peptide employing the erbB-2 and DF3 promoter elements in adenoviral vectors," *Cancer Gene Therapy*, 6::209-219, 1999.
Strader et al., "Structure and function of G protein-coupled receptors," *Annu. Rev. Biochem.*, 63:101-32, 1994.
Takakura et al., "Cloning of human telomerase catalytic subunit (hTERT) gene promoter and identification of proximal core promoter sequences essential for transcriptional activation in immortalized and cancer cells," *Cancer Res.*, 59(3):551-557, 1999.
Tearney et al., "Optical biopsy in human urologic tissue using optical coherence tomography," *J Urol.*, 157(5):1915-1919, 1997.
Umeoka et al., "Visualization of intrathoracically disseminated solid tumors in mice with optical imaging by telomerase-specific amplification of a transferred green flourescent protein gene," *Cancer Res.*, 64:6259-6265, 2004.

(56) References Cited

OTHER PUBLICATIONS

Uno et al., "Myristoylation of Fus1 protein is required for Fus1-mediated tumor suppressing activities in human lung cancer," *Proceedings of the Amer. Assoc. for Cancer Res.*, 44:75, 2003 (Abstract 397).

Uno et al., "Myristoylation of the fus1 protein is required for tumor suppression in human lung cancer cells," *Cancer Res.*, 64:2969-2976, 2004.

Verra et al., "Human telomerase reverse transcriptase-transduced human cytotoxic T cells suppress the growth of human melanoma in immunodeficient mice," *Cancer Res.*, 64:2153-61, 2004.

Verwijnen et al. "Molecular imaging and treatment of malignant gliomas following adenoviral transfer of the herpes simplex virus-thymidine kinase gene and the somatostatin receptor subtype 2 gene," *Cancer Biotherapy & Radiopharmaceuticals*, 19:111-120, 2004.

Wang et al., "Enhanced suicide gene therapy by chimeric tumor-specific promoter based on HSF1 transcriptional regulation," *FEBS Lett*, 546(3): 315-20, 2003.

Wirth et al., "A telomerase-dependent conditionally replicating adenovirus for selective treatment of cancer," *Cancer Research*, 63:3181-3188, 2003.

Zhang et al., "Gene therapy for malignant glioma using Sindbis vectors expressing a fusogenic membrane glycoprotein," *J. Gene Med.*, 6(10):1082, 2004.

Zhao et al., "Differential conjugation of tat peptide to superparamagnetic nanoparticles and its effect on cellular uptake," *Bioconjug. Chem.*, 13:840-844, 2002.

Zinn et al., "Noninvasive monitoring of gene transfer using reporter receptor imaged with a high-affinity peptide radiolabeled with $^{99m}$Tc or $^{188}$Re," *J. of Nuclear Med.*, 41:887-895, 2000.

Zinn et al., "Simultaneous evaluation of dual gene transfer to adherent cells by gamma-ray imaging," *Nuclear Med. Biol.*, 28:135-144, 2001.

Agha-Mohammadi and Lotze, "Regulatable systems: applications in gene therapy and replicating viruses," *J. Clin. Invest.*, 105:1177-1183, 2000.

Davis et al., "Oncolysis and suppression of tumor growth by a GFP-expressing oncolytic adenovirus controlled by an hTERT and CMV hybrid promoter," *Cancer Gene Therapy*, pp. 1-4, 2006.

Diaz et al., "Exchange of viral promoter/enhancer elements with heterologous regulatory sequences generates targeted hybrid long terminal repeat vectors for gene therapy of melanoma," *J. Virol.*, 72:789-795, 1998.

Fukazawa et al., "Development of a cancer-targeted tissue-specific promoter system," *Cancer Res.*, 64:363-369, 2004.

Hagstrom et al., "Improved muscle-derived expression of human coagulation factor IX from a skeletal actin/CMV hybrid enhancer/promoter," *Blood*, 95:2536-2542, 2000.

Horikawa et al., "Cloning and characterization of the promoter region of human telomerase reverse transcriptase gene," *Cancer Res.*, 59:826-830, 1999.

Majumdar et al., "The telomerase reverse transcriptase promoter drives efficacious tumor suicide gene therapy while preventing hepatotoxicity encountered with constitutive promoters," *Gene Therapy*, 8:568-578, 2001.

Omirulleh et al., "Activity of a chimeric promoter with the doubled CaMV 35S enhancer element in protoplast-derived cells and transgenic plants in maize," *Plant Mol. Biol.*, 21:415-428, 1993.

Wu et al., "A novel synthetic hTERT-Mini_CMV chimera promoter-driven tumor-selective and high-efficiency expression of transgene for systemic cancer gene therapy," *Proc. Amer. Assoc. Cancer Res.*, 46:3358, 2005.

* cited by examiner pLJ293/pKGB2/EGFP pLJ287/pKGB2/hTERT-EGFP pLJ296pKGB2/SSRT2A

HTMC PROMOTER AND VECTORS FOR THE TUMOR-SELECTIVE AND HIGH-EFFICIENT EXPRESSION OF CANCER THERAPEUTIC GENES

The present application is related to U.S. Provisional Patent Application 60/659,935, filed on Mar. 9, 2005, hereby incorporated by reference in its entirety.

The government owns rights in the present invention pursuant to grant number CA71618 from the National Institutes of Health and grant number DAMD17-02-1-0706 from the U.S. Department of Defense.

BACKGROUND OF THE INVENTION

1. Field of the Invention

The present invention relates generally to the fields of molecular biology, cancer biology, and gene therapy. More particularly, the invention concerns compositions comprising and methods utilizing novel promoters that include a tissue-selective promoter sequence and a second promoter sequence operatively coupled to the tissue-selective promoter sequence, wherein the second promoter sequence includes a minimal promoter sequence, preferably a minimal viral promoter sequence.

2. Description of Related Art

One of the major obstacles to successful gene therapy is the lack of an effective delivery system that can be targeted to a tissue of interest. For example, it would be beneficial to be able to target gene therapy for cancer to the tumor in the cancer patient. One means for tumor-targeted transgene expression is to control gene expression through the use of promoters that are selective for tumors.

One such promoter is the human telomerase reverse transcriptase (hTERT) promoter. hTERT is the catalytic subunit of telomerase. Telomerase is a ribonucleoprotein complex that is responsible for the complete replication of chromosomal ends (Blackburn, 1991). Many studies have demonstrated that the majority of malignant tumors express telomerase activity (Kim et al., 1996), whereas most normal cells do not (Shay and Wright, 1996). Three major components associated with telomerase activity in humans have been identified: (a) the RNA component [hTER (Feng et al., 1995)]; (b) the telomerase-associated protein [hTEP1 (Harrington et al., 1997)]; and (c) the telomerase catalytic unit or human telomerase reverse transcriptase [hTERT (Meyerson et al., 1997; Nakamura et al., 1997)]. Only hTER and hTERT, however, are required for the reconstitution of telomerase activity in vitro (Nakayama et al., 1998) and therefore represent the minimal catalytic core of telomerase in humans (Beattie et al., 1998).

The promoter region of hTERT has been cloned and characterized previously (Takakura et al., 1999). Telomerase-specific expression of cytotoxic or proapoptotic genes such as the diphtheria toxin A-chain, FADD, caspases, and Bax by the hTERT promoter has been successfully achieved and reporter in various gene transfer systems, such as plasmid and adenovirus (see, e.g., Abdul-Ghani et al., 2000; and Komata et al., 2001).

However, the transcription promoting strength of the hTERT promoter, like most other intrinsic mammalian promoters, is usually much weaker than commonly used viral promoters such as the CMV promoter and the SV40 early promoter. Consequently, it use for gene therapy is hampered by the problem of low transgene expression.

To overcome the weak transcription promoting capability of unmodififed hTERT promoter in mammalian cells in vitro and in vivo, some investigators have developed a binary adenoviral vector system wherein the hTERT promoter and transgene are placed under the control of the Ga14 gene or tetracycline responsive element (TRE) in a first vector (Gu et al., 2000; Gu et al., 2002). A second vector expresses an enhancer such as VP16 protein or Tet-On/Tet-Off transactivators to augment transgene expression from hTERT. However, the system is too complex and impractical for clinical application because of the deficiencies associated with the use of two separate vectors. In particular, the dual vector system is random and uncontrollable because it is difficult for both vectors to enter the same cell at the same time. Furthermore, it may potentially result in increased toxicity due to the use of multiple vectors and multiple therapeutically unrelated components and gene products involved in the system.

Therefore, there is the need for more effective tissue-selective promoters or improved methods of facilitating promoter function to allow for enhanced tissue-selective transgene expression. Promoter technology in this area would facilitate the clinical application and development of vectors for use in gene therapy as well as other technologies that require high transgene expression, such as reporter-based imaging modalities. Combining this technology into a single vector would help to diminish the toxicity associated with dual or multiple vectors.

SUMMARY OF THE INVENTION

The inventors have developed certain novel chimeric promoters that are tissue-selective and promote highly efficient expression of transgenes in vitro and in vivo. In particular, the inventors have developed certain novel chimeric promoters composed of a tissue-selective promoter sequence fused to a minimal viral promoter sequence, and methods utilizing these novel promoters. For example, a novel chimeric promoter has been developed that includes an hTERT sequence fused to a miniCMV (hTMC) promoter sequence, which was engineered by optimally fusing an essential hTERT promoter sequence with a mini-CMV promoter sequence. They have also developed methods of improving the function of a tissue-selective promoter. Using these promoters, the inventors are able to achieve both high tumor specificity and high transgene expression both in vitro and in vivo. As set forth herein, these promoters have broad application in methods of transferring a gene into a cell, such as for the purpose of treating a hyperproliferative disease in a subject or for imaging a reporter sequence in a cell.

Certain embodiments of the present invention generally pertain to promoters that include a tissue-selective promoter sequence and a second promoter sequence operatively coupled to the tissue selective promoter sequence, wherein the second promoter sequence includes a minimal viral promoter sequence wherein operatively coupling the tissue-selective promoter sequence to the second promoter sequence results in improved promoter function of the tissue-selective promoter sequence. A "promoter sequence" is a control sequence that is a region of a nucleic acid sequence at which initiation and rate of transcription are controlled. Promoter sequences are discussed in greater detail in the specification below.

A "tissue-selective promoter sequence" is defined herein to refer to a promoter sequence that is capable of driving transcription of a gene in one tissue while remaining largely "silent" or expressed at low relatively low levels in other tissue types. Tissue-specific promoter sequences are discussed in greater detail in the specification below. Any tissue-selective promoter sequence known to those of ordinary skill in the art is contemplated for inclusion in the promoter sequences of the present invention. Exemplary tissue-selective promoters include an hTERT promoter sequence, a CEA promoter sequence, a PSA promoter sequence, a probasin promoter sequence, a ARR2PB promoter sequence, or an AFP promoter sequence human alpha-lactalbumin promoter sequence, an ovine beta-lactoglobulin promoter sequence, a U6 promoter sequence, an H1 promoter sequence, a 7SL promoter sequence, a human Y promoter sequence, a human MRP-7-2 promoter sequence, an adenovirus VA1 promoter sequence, a human tRNA promoter sequence, a 5S ribosomal RNA promoter sequence, or a functional hybrid or a combination of any of these promoter sequences.

The tissue-selective promoter sequence may be active in any tissue type of a subject, whether human or other mammal. For example, the tissue-selective promoter may be active in heart, lung, esophagus, muscle, intestine, breast, prostate, stomach, bladder, liver, spleen, pancreas, kidney, neurons, myocytes, leukocytes, immortalized cells, neoplastic cells, tumor cells, cancer cells, duodenum, jejunum, ileum, cecum, colon, rectum, salivary glands, gall bladder, urinary bladder, trachea, larynx, pharynx, aorta, arteries, capillaries, veins, thymus, mandibular lymph node, mesenteric lymph node, bone marrow, pituitary gland, thyroid gland, parathyroid glands, adrenal glands, brain, cerebrum, cerebellum, medulla, pons, spinal cord, sciatic nerve, skeletal muscle, smooth muscle, bone, testes, epidiymides, prostate, seminal vesicles, penis, ovaries, uterus, mammary glands, vagina, skin, eyes, or optic nerve.

In certain embodiments, the tissue selective promoter sequence a tumor-selective promoter sequence. A tumor-selective promoter sequence is defined herein as a promoter sequence that is capable of driving transcription of a gene in tumor cell while remaining largely "silent" or expressed at low relatively low levels in other tissue types. For example, the tumor-selective promoter sequence may be an hTR promoter sequence, hTERT promoter sequence, CEA promoter sequence, a PSA promoter sequence, a probasin promoter sequence, a ARR2PB promoter sequence, or an AFP promoter sequence, MUC-1, mucin-like glycoprotein, C-erbB2/neu oncogene, Cyclo-oxygenase, E2F transcription factor 1, tyrosinase related protein, tyrosinase, or survivin.

In certain embodiments, the tissue-selective promoter sequence is a hypoxia-specific promoter sequence. A hypoxia-specific promoter sequence is defined herein as a promoter sequence that is capable of driving transcription of a gene in when the cell is exposed to hypoxic conditions while remaining largely "silent" or expressed at low relatively low levels in other tissue types under non-hypoxic conditions. Any hypoxia-specific promoter sequence known to those of ordinary skill in the art is contemplated for inclusion in the present invention. For example, the hypoxia-specific promoter sequence may be a hypoxic response element (HRE) or a hypoxia inducible factor. For example, the hypoxia inducible factor may be HIF-1alpha, HIF-2alpha, or HIF-3alpha.

In certain particular embodiments of the present invention, the tissue-selective promoter sequence is an hTERT promoter sequence. For example, the hTERT promoter sequence may be SEQ ID NO:1.

A minimal viral promoter sequence or a core promoter sequence is defined herein to refer to a portion of a promoter that includes a nucleotide sequence that maintains the ability to bind and locate a transactivator or a component of a transcription complex to a particular location in a nucleic acid. Promoter elements, particularly a TATA element, that are inactive or that have greatly reduced promoter activity in the absence of upstream activation are referred to as minimal or core promoters. In the presence of a suitable transcription factor, the minimal promoter functions to permit transcription. A minimal or core promoter thus consists only of all basal elements needed for transcription initiation, e.g., a TATA box and/or an initiator. Any minimal viral promoter sequence known to those of ordinary skill in the art is contemplated for inclusion in the promoter sequences of the present invention. The minimal viral promoter sequence, for example, can be an adenoviral promoter sequence, a baculoviral promoter sequence, a CMV promoter sequence, a parvovirus promoter sequence, a herpesvirus promoter sequence, a poxvirus promoter sequence, an adeno-associated virus promoter sequence, a semiliki forest virus promoter sequence, an SV40 promoter sequence, a vaccinia virus promoter sequence, or a retrovirus promoter sequence.

In certain particular embodiments, the promoter sequence is a mini-CMV promoter sequence. For example, the mini-CMV sequence can be SEQ ID NO:2. In some embodiments, the tissue-selective promoter sequence is an hTERT promoter sequence, and the second promoter sequence is a mini-CMV promoter sequence. For example, the promoter sequence may include SEQ ID NO:3, which includes an hTERT promoter sequence operatively coupled to a mini-CMV sequence.

Certain other embodiments of the present invention generally pertain to nucleic acids that include a promoter, wherein the promoter includes a tissue-selective promoter sequence, and a second promoter sequence operatively coupled to the tissue-selective promoter sequence, wherein said second promoter sequence comprises a minimal viral promoter sequence, wherein operatively coupling the tissue-selective promoter sequence to the second promoter sequence results in improved promoter function of the first promoter sequence. A "nucleic acid" as used herein will generally refer to a molecule (i.e., a strand) of DNA, RNA or a derivative or analog thereof, comprising a nucleobase. Nucleic acids are discussed in greater detail in the specification below. Any of the tissue-selective promoter sequences and minimal viral promoter sequences set forth above can be incorporated into the nucleic acid sequences of the present invention. As discussed above, the tissue-selective promoter sequence may, in certain embodiments, be further defined as a tumor-selective promoter sequence or a hypoxia-specific promoter sequence. In certain particular embodiments, the tissue-selective promoter sequence is an hTERT promoter sequence such as, for example, the sequence set forth in SEQ ID NO:1. Further, in some embodiments, the nucleic acids includes one or more additional promoter sequences that may or may not be operatively coupled to the tissue-selective promoter sequence.

In some embodiments of the present invention, the nucleic acid includes one or more genes operatively coupled to the promoter. Any gene known to those of ordinary skill in the art is contemplated for inclusion in the methods of delivering a gene to a cell. The term "gene" is used for simplicity to refer to a functional protein, polypeptide, or peptide-encoding unit. Genes are discussed in greater detail in the specification below. Any gene is contemplated in the nucleic acid sequences of the present invention. For example, the gene may be a therapeutic gene or selectable marker. A therapeutic gene is defined herein to refer to a gene which can be administered to a subject for the purpose of treating or preventing a disease. For example, a therapeutic gene can be a gene administered to a subject for treatment or prevention of a hyperproliferative disease. In certain particular embodiments, the hyperproliferative disease is cancer. The therapeutic gene may be, for example, a tumor suppressor gene, a gene that induces apoptosis, a gene encoding an enzyme, a gene encoding an antibody, or a gene encoding a hormone. Exemplary therapeutic genes include Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, FUS1, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, Gene 26 (CACNA2D2), PL6, Beta*(BLU), LUCA-1 (HYAL1), LUCA-2 (HYAL2), 123F2 (RASSF1), 101F6, Gene 21 (NPRL2), SEM A3 or MCC. In certain particular embodiments, the therapeutic gene is FUS1.

A selectable marker is defined herein to refer to a nucleic acid sequence that when expressed confers an identifiable characteristic to the cell permitting easy identification, isolation and/or selection of cells containing the selectable marker from cells without the selectable marker. Any selectable marker known to those of ordinary skill in the art is contemplated for inclusion as a selectable marker in the nucleic acids of the present invention. For example, the selectable marker may be a drug selection marker, an enzyme, or an immunologic marker. In some embodiments, the nucleic acid of the present invention is comprised in a plasmid.

Some embodiments of the nucleic acid sequences of the present invention includes one or more reporter sequences operatively coupled to the promoter sequence. A "reporter," "reporter gene" or "reporter sequence" as used herein refers to any genetic sequence or encoded polypeptide sequence that is detectable and distinguishable from other genetic sequences or encoded polypeptides present in cells. Exemplary reporter sequences include a polynucleotide encoding a somatostatin receptor amino acid sequence, a sodium iodide symporter amino acid sequence, a eukaryotic green fluorescence protein amino acid sequence, a red fluorescence protein amino acid sequence, a luciferase amino acid sequence, a β-galactosidase amino acid sequence, or a thymidine kinase amino acid sequence. The somatostatin receptor amino acid sequence may be, for example, a recombinant somatostatin receptor amino acid sequence, a somatostatin type 2 receptor amino acid sequence, or mutated somatostatin type 2 receptor amino acid sequence. In certain embodiments, the somatostatin type 2 receptor amino acid sequence is a somatostatin receptor type 2A amino acid sequence.

The reporter sequence may be coupled with IRES to a second gene. IRES are discussed elsewhere in this specification. The second gene can be any gene known to those or ordinary skill in the art, including any of the genes discussed above. The gene may or may not be operatively coupled to a second reporter. The second reporter can be any reporter known to those of ordinary skill in the art, including those reporters discussed above. For example, the second reporter may be a somatostatin receptor amino acid sequence, a sodium iodide symporter amino acid sequence, a luciferase amino acid sequence, a eukaryotical green fluorescence protein amino acid sequence, or a thymidine kinase amino acid sequence. In some embodiments, the second gene comprises a selectable marker or a therapeutic gene. Therapeutic genes are discussed above, and elsewhere in this specification. In certain embodiments of the nucleic acids of the present invention, the tissue-selective promoter sequence is an hTERT promoter sequence, the second promoter sequence is a mini-CMV promoter sequence, and the promoter is operatively coupled to a gene encoding FUS1. In these embodiments, the nucleic acid sequence may or may not be comprised in a plasmid.

The present invention also generally pertains to compositions that include a promoter, wherein the promoter includes any of the promoters of the present invention set forth above. The compositions of the present invention may or may not include a delivery vehicle for delivery of the promoter to a cell in a subject. A delivery vehicle is defined herein to refer to any agent that can facilitate the delivery of nucleic acid into the cell. The cell can be any cell of a subject. The subject can be any subject, such as a mammal. In certain particular embodiments, the subject is a human. One of ordinary skill in the art would be familiar with delivery vehicles for use in facilitating the delivery of a nucleic acid sequence into a cell in a subject. For example, the delivery vehicle may be a nucleic acid, a plasmid, a viral vector, a prokaryotic cell, a eukaryotic cell, or a lipid. Any viral vector is contemplated for inclusion in the compositions of the present invention. For example, the viral vector may be an adenoviral vector, a retroviral vector, a vaccinia viral vector, an adeno-associated viral vector, or a poxviral vector. In certain particular embodiments of the present invention, the viral vector is an adenovirus. Furthermore, any lipid known by those of ordinary skill in the art to be of use as a delivery vehicle is contemplated. In some embodiments, the lipid is comprised in a liposome. The liposome can be any liposome known to those of ordinary skill in the art to be suitable for use as a delivery vehicle. For example, the liposome may include cationic lipid, such as DOTAP:Chol. The liposome may be comprised in nanoparticles, such as DOTAP:Chol nanoparticles. A nanoparticle is defined herein to refer to particles have diameters below 1 micrometer in diameter.

Certain further embodiments of the present invention generally pertain to compositions that include any of the nucleic acids set forth above. The compositions that include any of the nucleic acids set forth above may further include a delivery vehicle, wherein the delivery vehicle for delivery of the nucleic acid to a cell in a subject. Any of the delivery vehicles set forth above is suitable for inclusion in these embodiments of the present invention. For example, in some embodiments, the delivery vehicle is a viral vector or a lipid, as discussed above.

Other embodiments of the present invention generally pertain to methods of improving the function of a tissue-selective promoter, that include (1) selecting a tissue-selective promoter sequence; (2) selecting a second promoter sequence, wherein said second promoter sequence includes a minimal viral promoter sequence; and (3) operatively coupling the tissue-selective promoter sequence to the second promoter sequence, wherein operatively coupling the tissue-selective promoter sequence to the second promoter sequence results in improved function of the tissue-selective promoter sequence. Any of the tissue-selective promoter sequences discussed above is suitable for use in these embodiments of the present invention. For example, as discussed above, the tissue-selective promoter sequence may be an hTERT promoter sequence, a CEA promoter sequence, a PSA promoter sequence, a probasin promoter sequence, a ARR2PB promoter sequence, an AFP promoter sequence, a human alpha-lactalbumin promoter sequence, an ovine beta-lactoglobulin promoter sequence, a U6 promoter sequence, an H1 promoter sequence, a 7SL promoter sequence, a human Y promoter sequence, a human MRP-7-2 promoter sequence, an adenovirus VA1 promoter sequence, a human tRNA promoter sequence, a 5S ribosomal RNA promoter sequence, or a functional hybrid or a combination of any of these promoter sequences. The tissue-selective promoter sequence may be any hypoxia-specific promoter sequence, as discussed above. In certain particular embodiments of the methods of the present invention, the tissue-selective sequence is an hTERT promoter sequence, such as SEQ ID NO:1. The minimal viral promoter sequence of the present methods can include any of the minimal viral promoter sequences discussed above. For example, in certain particular embodiments of the methods of the present invention, the minimal viral promoter sequence is a mini-CMV promoter sequence. For example, the mini-CMV sequence may be SEQ ID NO:2.

In some embodiments, the tissue-selective promoter sequence is an hTERT promoter sequence, and wherein the second promoter sequence is a mini-CMV promoter sequence. For example, the promoter may include SEQ ID NO:3.

Still further embodiments of the present invention generally pertain to methods of delivering a gene into a cell, that include: (1) preparing a composition comprising a gene operatively coupled to a promoter, wherein the promoter is any of the novel promoters of the present invention set forth above; and (2) contacting the composition with the cell, wherein the contacting results in delivery of the gene into the cell. The cell can be any cell of a subject. Further, as discussed above, the subject can be any subject, such as a mammal. In certain particular embodiments, the subject is a human. For example, the human can be a patient with a disease, such as a hyperproliferative disease. For example, the hyperproliferative disease may be cancer. Hyperproliferative diseases, such as cancer, are discussed in greater detail in the specification below.

The composition, in some embodiments, includes a delivery vehicle for use in facilitating delivery of the gene into a cell. Any of the delivery vehicles discussed above is suitable for use in these embodiments of the present invention. For example, the delivery vehicle can be any of the viral vectors or lipids set forth above. Viral vectors and lipids are also discussed in greater detail below in the specification. In certain particular embodiments, the viral vector is an adenoviral vector. For example, the vector may be a protamine-complexed viral vector.

Still further embodiments of the present invention generally pertain to methods of treating a subject with a hyperproliferative disease, that include: (1) obtaining a pharmaceutical composition of a polynucleotide that includes any of the novel nucleic acid sequences set forth above; and (2) administering a pharmaceutically effective amount of the composition to the subject. As discussed above, the subject can be any subject, such as a mammal. The mammal may be a human, such as a patient with a disease. The disease can be any disease that can afflict a subject. In certain particular embodiments, the subject is a human, and the disease is a hyperproliferative disease such as cancer. The cancer may be any cancer, such breast cancer, lung cancer, prostate cancer, ovarian cancer, brain cancer, liver cancer, cervical cancer, colon cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia. In certain particular embodiments, the cancer is lung cancer. In some embodiments, the subject is undergoing secondary anticancer therapy. Any secondary anti-cancer therapy known to those of ordinary skill in the art is contemplated, such as chemotherapy, surgical therapy, radiation therapy, immunotherapy, or additional gene therapy. Secondary anticancer therapy is discussed in greater detail in the specification below.

The present invention also generally pertains to methods of imaging a cell, that include: (1) contacting the cell with a composition that includes any of the nucleic acids set forth above, wherein the promoter is operatively coupled to a reporter amino acid sequence; and (2) detecting cellular expression of the reporter sequence by measuring a signal derived from the reporter. The term "reporter," "reporter gene" or "reporter sequence" as used herein refers to any genetic sequence or encoded polypeptide sequence that is detectable and distinguishable from other genetic sequences or encoded polypeptides present in cells. Reporters are discussed in greater detail in the specification below. The cell can be any cell. In certain embodiments, the cell is a cell in a subject, such as a mammal. The mammal may be a human. The human may be a patient with a disease, such as a hyperproliferative disease. For example, the hyperproliferative disease may be cancer. In some embodiments, for example, the cell is in a subject, and the method of imaging a cell is further defined as a method of imaging a tissue in a subject. A "tissue" is defined herein to refer to an aggregation of morpholigically similar cells and associated intercellular matter that together perform specific functions in the body. For example, the tissue may be lung tissue, renal tissue, breast tissue, and so forth. The tissue may also be comprised of neoplastic cells, such as in a cancerous tumor. In certain embodiments of the present methods of imaging, the cell is a cancer cell, and wherein the method of imaging a cell is further defined as a method of imaging a tumor in a patient with cancer.

The reporter can be any reporter known to those of ordinary skill in the art. For example, the reporter may be an enzyme amino acid sequence, a receptor amino acid sequence, or a ribozyme RNA sequence. For example, the reporter amino acid sequence may be a recombinant seven transmembrane G-protein associated receptor amino acid sequence, a thymidine kinase amino acid sequence, a dopamine receptor amino acid sequence, an endothelial growth factor receptor (EGFR) amino acid sequence, a plasminogen amino acid sequence, a urokinase-type plasminogen activator receptor (uPAR) amino acid sequence, a hormone receptor amino acid sequence, or a sodium/iodide symporter amino acid sequence. In certain particular embodiments of the present invention, the reporter amino acid sequence is a recombinant seven transmembrane G-protein associated receptor (GPCR) amino acid sequence. Any recombinant GPCR amino acid sequence known to those of ordinary skill in the art is contemplated for use as a reporter. For example, the GPCR may be an acetylcholine receptor: M1, M2, M3, M4, or M5; adenosine receptor: A1; A2A; A2B; or A3; adrenoceptors: alpha1A, alpha1B, alpha1D, alpha2A, alpha2B, alpha2C beta1, beta2, or beta3; angiotensin receptors: AT1, or AT2; bombesin receptors: BB1, BB2, or BB3; bradykinin receptors: B1, B2, calcitonin, Ainilin, CGRP, or adrenomedullin receptors; cannabinoid receptors: CB1, or CB2; chemokine receptors: CCR1, CCR2, CCR3, CCR4, CCR5, CCR6, CCR7, CCR8, CCR9, CCR10, CXCR1, CXCR2, CXCR3, CXCR4, CXCR5, CX3CR1, or XCR1; chemotactic receptors: C3a, C5a, or fMLP; cholecystokinin and gastrin receptors: CCK1, or CCK2; corticotropin-releasing factor receptors: CRF1, or CRF2; dopamine receptors: D1, D2, D3, D4, or D5; endothelin receptors: ET(A) or ET(B); galanin receptors: GAL1, GAL2, or GAL3; glutamate receptors: mgl1, mgl2, mgl3, mgl4, mgl5, mgl6, mgl7, or mgl8; glycoprotein hormone receptors: FSH, LSH, or TSH; histamine receptors:

H1, H2, H3, or H4; 5-HT receptors: 5-HT1A, 5-HT1B, 5-HT1D, 5-HT1B, 5-HT1F, 5HT2A, 5-HT2F, 5-HT2C, 5-HT3, 5-HT4, 5-HT5A, 5-HT5B, 5-HT6, or 5-HT7; leukotriene receptors: BLT, CysLT1, or CysLT2; lysophospholipid receptors: edg1, edg2, edg3, or edg4; melanocorlin receptors: MC1; MC2; MC3; MC4, or MC5; melatonin receptors: MT1, MT2, or MT3; neuropeptide Y receptors: Y1, Y2, Y4, Y5, or Y6; neurotension receptors: NTS1, or NTS2; opioids: DOP, KOP, MOP, or NOP; P2Y receptors: P2Y1, P2Y2, P2Y4, P2Y6, P2Y11, or P2Y12); peroxisome proliferators: PPAR-alpha, PPAR-beta, or PPAR-gamma; prostanoid receptors: DP, FP, IP, TP, EP1, EP2, EP3, or EP4; protease-activated receptors: PAR1, PAR2, PAR3, or PAR4; Somatostatin receptors: SSTR1, SSTR2, SSTR2A, SSTR3, SSTR4, or SSTR5; tachykinin receptors: NK1, NK2, or NK3; thyrotropin-releasing hormone receptors: TRH1, or TRH2; urotensin-II receptor; vasoactivate intestinal peptide or pituitary adenylate cyclase activating peptide receptors: VPAC1, VPAC2, or PAC1; or vasopressin or oxytocin receptors: V1a, V1b, V2, or OT.

In certain particular embodiments of the present methods of imaging, the recombinant GPCR amino acid sequence is a recombinant somatostatin receptor amino acid sequence, a recombinant somatostatin type 2 receptor amino acid sequence, or a mutated somatostatin type 2 receptor amino acid sequence. For example, the recombinant somatostatin type 2 receptor amino acid sequence may be a recombinant somatostatin type 2A receptor amino acid sequence.

In certain particular embodiments of the present invention, the recombinant GPCR amino acid sequence comprises a nucleic acid encoding a truncated recombinant GPCR. The truncation can be a truncation at either the N-terminus or C-terminus. In some embodiments, the truncation is a carboxy terminal truncation. The truncation may or may not result in alteration of function of the GPCR as a GPCR. For example, in some embodiments, the truncation results in alteration of internalization and/or signaling of the recombinant GPCR amino acid sequence.

In some embodiments of the present invention, the nucleic acid encoding the reporter amino acid sequence includes a heterologous leader sequence at the N-terminus or C-terminus of the reporter amino acid sequence, wherein the leader sequence guides the reporter amino acid sequence to a particular subcellular location. In further embodiments of the present invention, the nucleic acid encoding the reporter amino acid sequence further includes a protein tag fused to the N-terminal end or C-terminal end of the reporter amino acid sequence. The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation, localization, and/or identification by procedures such as affinity or immunoaffinity chromatography, immunohistochemistry, or non-invasive detection methods described herein. Chemical tag moieties include such molecules as biotin, which may be added to either nucleic acids or proteins to facilitate isolation or detection by interaction with avidin reagents, and the like. Numerous other tag moieties are known to, and can be envisioned by the trained artisan, and are contemplated to be within the scope of this definition. The protein tag may, in some embodiments, have enzymatic activity. In some embodiments of the present invention, the protein tag has enzymatic activity. Examples of such protein tags include hemagglutinin A, beta-galactosidase, thymidine kinase, transferrin, myc-tag, VP16, (His)$_6$tag, or chloramphenicol acetyl transferase.

In certain particular embodiments of the present invention, the imaging is performed intraoperatively on a subject. The subject can be undergoing surgery for any reason, such as for removal of diseased tissue. For example, in some embodiments of the present invention on a patient undergoing surgical resection of a tumor.

In further embodiments of the methods of imaging of the present invention, a gene is operatively coupled to the promoter, and the method of imaging a cell is further defined as a method of delivering a gene to a cell. Thus, for example, imaging of a cell and gene delivery to a cell can be performed concurrently in certain embodiments of the present invention.

For example, the gene may be any of the genes discussed above in the context of other embodiments of the present invention. For example, the gene may be is a therapeutic gene. As discussed above, examples of therapeutic genes include tumor suppressor genes, genes that induces apoptosis, genes encoding an enzyme, genes encoding an antibody, or genes encoding a hormone. For example, the therapeutic gene may be Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, FUS1, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, Gene 26 (CACNA2D2), PL6, Beta*(BLU), LUCA-1 (HYAL1), LUCA-2 (HYAL2), 123F2 (RASSF1), 101F6, Gene 21 (NPRL2), SEM A3 or MCC. In certain particular embodiments of the present invention, the therapeutic gene is FUS1.

As discussed above, the methods of imaging can further include methods of delivering a gene into a cell. In some embodiments of the present invention, the reporter is imaged to track gene delivery into a cell, such as gene delivery into diseased tissues of a subject. Thus, in certain embodiments of the present invention, the method of imaging is further defined as a method of measuring biodistribution of a gene in a subject following administration of the gene to the subject. In some embodiments, the method of imaging is further defined as a method to measure response to administration of a therapeutic gene in a subject.

Any method of measuring a signal known to those of ordinary skill in the art is contemplated for inclusion in the methods of imaging of the present invention. Exemplary methods of imaging include performing fluorescence imaging analysis, immunohistochemical analysis, chemiluminescence imaging, optical imaging, magnetic resonance imaging, or radioimaging. Methods of measuring a signal are discussed in detail elsewhere in this specification. Other examples include CT imaging and ultrasound. Any method of radioimaging known to those of ordinary skill in the art is contemplated as a method of measuring a signal to be employed in the context of the present invention. For example, in some embodiments, radioimaging is further defined as gamma camera imaging. One of ordinary skill in the art would be very familiar with gamma camera imaging. In certain particular embodiments, measuring a signal is further defined as gamma-camera imaging with the $^{111}$In-octreotide-somatostatin receptor type 2A (SSRT2A) reporter system. Furthermore, one of ordinary skill in the art would be familiar with magnetic resonance imaging. In certain particular embodiments, measuring a signal is further defined as magnetic resonance imaging using a super-paramagnetic iron oxide (SPIO)-octreotide-SSTR2A reporter and a contrast enhancer system. SPIO is a contrast agent for MRI and is used to enhance resolution of tumor tissues by enhancing the contrast to the normal tissue background (See Artemov et al., 2003; Zhao et al., 2002; Gupta and Curtis, 2004, each of which is herein specifically incorporated by reference). One of ordinary skill in the art would be familiar with the employment of contrast agents in imaging, such as in magnetic resonance imaging. Use of contrast agents in imaging and exemplary contrast agents are discussed at in greater detail in the specification below.

Certain aspects of the invention include methods of enhancing tissue-selective promoter function to facilitate the development of other technologies, such as imaging directed to a tissue of interest. Reviewed in Umeoka et al., 2004. A variety of imaging technologies are available for imaging tumors. These imaging technologies can be applied in cancer detection, diagnosis, and treatment monitoring. Improvements in methods of external imaging such as computed tomography, magnetic resonance imaging, and ultrasound techniques have increased the sensitivity for visualizing tumors and metastases (Tearney et al., 1997; MacDonald and Hansell, 2003). A limiting factor in structural and anatomical imaging, however, is the inability to specifically identify malignant tissues. Histopathological examination is still the most effective method for the detection of neoplastic lesions. Thus, imaging that is tumor-selective would be of considerable value in the treatment of human cancer because it would allow for the localization of tumors without microscopic analysis. In particular, if tumors too small for direct visual detection could be imaged in situ, surgeons could precisely excise tumors with appropriate surgical margins. These forms of imaging require an appropriate marker that is tumor-selective. Methods to improve the usefulness of tissue-selective promoters as discussed above can be applied in the development of improved methods of tissue-selective imaging.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 16A. Lung H417 tumors were established by intrathoracic injection of 1×10$^6$ N417 cells in nude mice. Mice were treated with various EGFP-lipoplexes (20 µg DNA:40 nmol DOTAP: Cholesterol/mouse) by i.v. injection. Animals were killed 48 hours after injection and fresh frozen samples of tumor, kidney, spleen, lung, and liver were prepared immediately. Frozen sections were fixed in 4% paraformaldehyde and expression of EGFP was examined immediately under a fluorescence microscope. hTMC, human TERT-mini-CMV promoter. FIG. 16B. Quantification of EGFP expression in tumor and normal mouse tissues by FACS analysis.

FIG. 17A: Immunofluorescence image analysis of SSRT2A expression in HT1080 transfectant. FIG. 17B: Gamma-camera image of nude mouse bearing s.c. tumors inoculated from corresponding SSRT2A-expressing (A, B, and C of FIG. 17A) and non-expressing (FIG. 17D) cells shown in FIG. 17A. Animals were i.v. injected with $^{111}$In-octreotide (13 MBq) and imaged 24 h later. FIG. 17C: Coexpression of SSRT2A (green) and FUS1 (red) in pLJ290/FUS1IRES-SSRT2A plasmid transfected H1299 cells. FIG. 17D: Correlation of radiotracer uptake by tumors. % ID/g=% injected dose per gram.

DESCRIPTION OF ILLUSTRATIVE EMBODIMENTS

Figure 1:
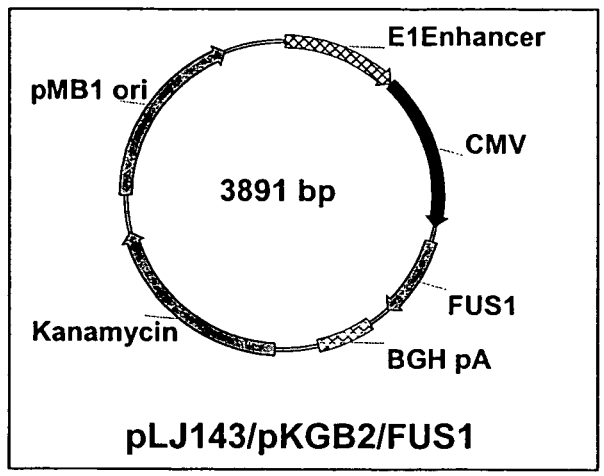
FIG. 1. Diagram of plasmid vector pLJ143/KGB2/FUS1.

One of the major obstacles to successful cancer gene therapy is the lack of an effective delivery system that can be specifically targeted to tumors. One means for tumor-targeted transgene expression is to control transgene expression via tumor-specific promoters. Human telomerase reverse transcriptase (hTERT) is the catalytic subunit of telomerase, which is highly active in immortalized cells and >85% of human cancers but is quiescent in most normal somatic cells. The hTERT promoter has been cloned and shown to be capable of targeting transgene expression in tumors but not in normal cells. However, the transcription-promoting strength of hTERT promoter, like most other intrinsic mammalian promoters, is much weaker than commonly used viral promoters such as the CMV and SV40 early promoters. Consequently, its use for cancer gene therapy is hampered by the problem of low transgene expression. To circumvent these problems, the inventors have developed certain novel chimeric or hybrid promoters that include a tissue-selective promoter sequence and a second promoter sequence operatively coupled to the tissue-selective promoter sequence, wherein the second promoter sequence includes a minimal viral promoter sequence. They have also developed certain novel methods of improving the function of a tissue-selective promoter that involve operatively coupling a tissue-selective promoter sequence with a second promoter sequence, wherein the second promoter sequence comprises a minimal viral promoter sequence. The novel promoters set forth herein can be applied in methods of transferring a gene into a cell, such as for the treatment of a hyperproliferative disease in a subject or for the purpose of imaging a cell, such as a cell in a subject. The novel promoters set forth herein can be applied in any method where improved transgene expression would be beneficial.

A. Promoters and Nucleic Acids that Include Promoters

Nucleic acids of the invention include chimeric or hybrid promoters comprising a tissue-selective promoter sequence and a second promoter sequence operatively coupled to the tissue-selective promoter sequence, wherein the second promoter sequence includes a minimal promoter sequence, preferably a minimal viral promoter sequence. The chimeric promoter sequence may be used in conjunction with other nucleic acid elements of the invention to construct the various nucleic acid vectors and nucleic acid vector systems described herein.

1. Nucleic Acids

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule The term "vector" is used to refer to a carrier into which a nucleic acid sequence can be inserted for introduction into a cell where it can be replicated. The term "expression vector" or "nucleic acid vector" refers to a vector containing a nucleic acid sequence or "cassette" coding for at least part of a gene product capable of being transcribed and "regulatory" or "control" sequences, which refer to nucleic acid sequences necessary for the transcription and possibly translation of an operably linked coding sequence in a particular host cell. In addition to control sequences that govern transcription and translation, expression vectors may contain nucleic acid sequences that serve other functions as well.

2. Promoter Sequences

A "promoter sequence" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence. Together, an appropriate promoter or promoter/enhancer combination, and a gene of interest, comprise an expression cassette. One or more expression cassettes may be present in a given nucleic acid vector or expression vector. In certain aspects, one expression cassette may encode a transactivator that interacts with a promoter of a second expression cassette. The one or more expression cassettes may be present on the same and/or different expression vector.

A promoter may be one naturally associated with a gene or sequence, as may be obtained by isolating a portion the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. In certain aspect of the invention a heterologous promoter may be a chimeric promoter, where elements of two or more endogenous, heterologous or synthetic promoter sequences are operatively coupled to produce a recombinant promoter.

A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Such promoters may be used to drive reporter expression, e.g., β-galactosidase or luciferase to name a few. Furthermore, it is contemplated the control sequences that direct transcription and/or expression of sequences within non-nuclear organelles such as mitochondria, chloroplasts, and the like, can be employed as well.

A promoter and/or enhancer will typically be used that effectively directs the expression of the DNA segment in a cell type, organelle, and organism chosen for expression. Those of skill in the art of molecular biology generally know the use of promoters, enhancers, and cell type combinations for protein expression, for example, see Sambrook et al., (1989), incorporated herein by reference. The promoters employed may be constitutive, tissue-specific, inducible, and/or useful under the appropriate conditions to direct expression of the introduced DNA segment, such as is advantageous in the production of recombinant proteins and/or peptides. The promoter may be heterologous or endogenous or a combination thereof.

a. Tissue-Selective Promoter Sequences

A promoter may be functional in a variety of tissue types and in several different species of organisms, or its function may be restricted to a particular species and/or a particular tissue or cell type. Further, a promoter may be constitutively active, or it may be selectively activated by certain substances (e.g., a tissue-specific factor), under certain conditions (e.g., hypoxia, or the presence of an enhancer element in the expression cassette containing the promoter), or during certain developmental stages of the organism (e.g., active in fetus, silent in adult).

Promoters useful in the practice of the present invention are preferably tissue-specific—that is, they are capable of driving transcription of a gene in one tissue while remaining largely "silent" or expressed at low relatively low levels in other tissue types. It will be understood, however, that tissue-specific or tissue-selective promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the present invention typically has a selectivity ratio of greater than about 2, 3, 4, or 5. Preferably, the selectivity ratio is greater than about 10 or 15.

It will be further understood that certain promoters, while not restricted in activity to a single tissue type, may nevertheless show selectivity in that they may be active in one group of tissues, and less active or silent in another group. Such promoters are also termed "tissue specific" or "tissue selective," and are contemplated for use with the present invention. For example, promoters that are active in a variety of tumor cells may be therapeutically useful in treating cancer, which may effect any of a number of different regions of the body.

Tissue-specific promoters may be derived, for example, from promoter regions of genes that are differentially expressed in different tissues or at different stages of growth or in cells that are hyperplastic.

The level of expression of a gene under the control of a particular promoter can be modulated by manipulating the promoter region. For example, different domains within a promoter region may possess different gene-regulatory activities. The roles of these different regions are typically assessed using vector constructs having different variants of the promoter with specific regions deleted (i.e., deletion analysis). Vectors used for such experiments typically contains a reporter sequence, which is used to determine the activity of each promoter variant under different conditions. Application of such a deletion analysis enables the identification of promoter sequences containing desirable activities and thus identifying a particular promoter domain, including core promoter elements. This approach may be used to identify, for example, the smallest region capable of conferring tissue specificity, or the smallest region conferring a robust transcriptional response when combined with other promoter elements, such as but not limited to the core CMV promoter, mini-CMV.

A number of tissue specific promoters, described herein, may be particularly advantageous in practicing the present invention. In most instances, these promoters may be isolated as convenient restriction digest fragments suitable for cloning into a selected vector. In certain aspects the invention includes, but is not limited to the hTERT promoter. Alternatively, promoter fragments may be isolated using the polymerase chain reaction or by oligonucleotide synthesis. Cloning of these promoter fragments may be facilitated by incorporating restriction sites at the 5' ends of the primers.

One of ordinary skill in the art would be familiar with the various types of tissue-selective promoter sequences that can be included in the context of the present invention. An exemplary list of these promoters is included in Table 1.

Table 1 lists non-limiting examples of elements/promoters that can be employed as a source of tissue-selective promoter sequences, in the context of the present invention.

TABLE 1

PROMOTER AND/OR ENHANCER

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |

TABLE 1-continued

| Promoter/Enhancer | References |
|---|---|
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al, 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| α₁-Antitrypsin | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 | b. Methods of Operatively Coupling Promoter Sequences

The term "promoter" is used interchangeably with "promoter element" and "promoter sequence." Likewise, the term "enhancer" is used interchangeably with "enhancer element" and "enhancer sequence." Promoters may be coupled with other promoters, promoter elements, and/or regulatory sequences/elements which, when bound to appropriate intracellular regulatory factors, enhance ("enhancers") or repress ("repressors") promoter-dependent transcription. A promoter, enhancer, or repressor, is said to be "operably linked" to a transgene when such element(s) control(s) or affect(s) transgene transcription rate or efficiency. For example, a promoter sequence located proximally to the 5' end of a transgene coding sequence is usually operably linked with the transgene. As used herein, term "regulatory elements" is used interchangeably with "regulatory sequences" and refers to promoters, enhancers, and other expression control elements, or any combination of such elements.

Promoters are positioned 5' (upstream) to the genes that they control. Many eukaryotic promoters contain two types of recognition sequences: TATA box and the upstream promoter elements. The TATA box, located 25-30 bp upstream of the transcription initiation site, is thought to be involved in directing RNA polymerase II to begin RNA synthesis as the correct site. In contrast, the upstream promoter elements determine the rate at which transcription is initiated. These elements can act regardless of their orientation, but they must be located within 100 to 200 bp upstream of the TATA box.

Enhancer elements can stimulate transcription up to 1000fold from linked homologous or heterologous promoters. Enhancer elements often remain active even if their orientation is reversed (Li et al., J. Bio. Chem. 1990, 266: 6562-6570). Furthermore, unlike promoter elements, enhancers can be active when placed downstream from the transcription initiation site, e.g., within an intron, or even at a considerable distance from the promoter (Yutzey et al., Mol. and Cell. Bio. 1989, 9:1397-1405).

As is known in the art, some variation in this distance can be accommodated without loss of promoter function. Similarly, the positioning of regulatory elements with respect to the transgene may vary significantly without loss of function. Multiple copies of regulatory elements can act in concert. Typically, an expression vector comprises one or more enhancer sequences followed by, in the 5' to 3' direction, a promoter sequence, all operably linked to a transgene followed by a polyadenylation sequence.

3. Genes

Certain embodiments of the present invention pertain to nucleic acid sequences that include one of the novel promoter sequences set forth herein, operatively coupled to one or more genes of interest. Certain other embodiments of the present invention pertain to methods of imaging a cell, wherein the methods are further defined as methods of delivering a gene to a cell. In these embodiments, the gene is operatively coupled to the promoter. Any gene known to those of ordinary skill in the art is contemplated for inclusion in the methods of delivering a gene to a cell. The term "gene" is used for simplicity to refer to a functional protein, polypeptide, or peptide-encoding unit.

In certain embodiments of the present invention, the gene is a therapeutic gene. A "therapeutic gene" is a gene which can be administered to a subject for the purpose of treating or preventing a disease. For example, a therapeutic gene can be a gene administered to a subject for treatment or prevention of cancer. Examples of therapeutic genes include, but are not limited to, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, Rb, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

In certain embodiments of the present invention, the therapeutic gene is a tumor suppressor gene. A tumor suppressor gene is a gene that, when present in a cell, reduces the tumorigenicity, malignancy, or hyperproliferative phenotype of the cell. This definition includes both the full length nucleic acid sequence of the tumor suppressor gene, as well as non-full length sequences of any length derived from the full length sequences. It being further understood that the sequence includes the degenerate codons of the native sequence or sequences which may be introduced to provide codon preference in a specific host cell.

Examples of tumor suppressor nucleic acids within this definition include, but are not limited to APC, CYLD, HIN-1, KRAS2b, p16, p19, p21, p27, p27mt, p53, p57, p73, PTEN, Rb, Uteroglobin, Skp2, BRCA-1, BRCA-2, CHK2, CDKN2A, DCC, DPC4, MADR2/JV18, MEN1, MEN2, MTS1, NF1, NF2, VHL, WRN, WT1, CFTR, C-CAM, CTS-1, zac1, scFV, ras, MMAC1, FCC, MCC, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide and FUS1. Chromosome 3p21.3 genes, such as FUS1, are discussed in greater detail in U.S. Patent Application Publication No. 20020164715, which is herein specifically incorporated by reference in its entirety.

Other exemplary tumor suppressor genes are described in a database of tumor suppressor genes at www.cise.ufl.edu/~yy1/HTML-TSGDB/Homepage.html. This database is herein specifically incorporated by reference into this and all other sections of the present application. Nucleic acids encoding tumor suppressor genes, as discussed above, include tumor suppressor genes, or nucleic acids derived therefrom (e.g., cDNAs, cRNAs, mRNAs, and subsequences thereof encoding active fragments of the respective tumor suppressor amino acid sequences), as well as vectors comprising these sequences. One of ordinary skill in the art would be familiar with tumor suppressor genes that can be applied in the present invention.

In certain embodiments of the present invention, the therapeutic gene is a gene that induces apoptosis (i.e., a pro-apoptotic gene). A "pro-apoptotic gene amino acid sequence" refers to a polypeptide that, when present in a cell, induces or promotes apoptosis. The present invention contemplates inclusion of any pro-apoptotic gene known to those of ordinary skill in the art. Exemplary pro-apoptotic genes include CD95, caspase-3, Bax, Bag-1, CRADD, TSSC3, bax, hid, Bak, MKP-7, PERP, bad, bcl-2, MST1, bbc3, Sax, BIK, BID, and mda7. Information regarding mda7 can be found, for example, in U.S. Pat. App. Publication Nos. 20050250127, 20040009939, 20030225025, and 20020183271, each of which is herein specifically incorporated by reference in its entirety. One of ordinary skill in the art would be familiar with pro-apoptotic genes, and other such genes not specifically set forth herein that can be applied in the methods and compositions of the present invention.

The therapeutic gene can also be a gene encoding a cytokine. The term 'cytokine' is a generic term for proteins released by one cell population which act on another cell as intercellular mediators. A "cytokine" refers to a polypeptide that, when present in a cell, maintains some or all of the function of a cytokine. This definition includes full-length as well as non-full length sequences of any length derived from the full length sequences. It being further understood, as discussed above, that the sequence includes the degenerate codons of the native sequence or sequences which may be introduced to provide codon preference in a specific host cell.

Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-.alpha. and .beta.; mullerian-inhibiting substance; mouse gonadotropin-associated peptide; inhibin; activin; vascular endothelial growth factor; integrin; thrombopoietin (TPO); nerve growth factors such as NGF-.beta.; platelet-growth factor; transforming growth factors (TGFs) such as TGF-.alpha. and TGF-.beta.; insulin-like growth factor-I and -II; erythropoietin (EPO); osteoinductive factors; interferons such as interferon-α, -β, and γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1.alpha., IL-2, IL-3, IL-4, IL-5, IL-6, IL-7, IL-8, IL-9, IL-11, IL-12; IL-13, IL-14, IL-15, IL-16, IL-17, IL-18, LIF, G-CSF, GM-CSF, M-CSF, EPO, kit-ligand or FLT-3.

Another example of a cytokine is IL-10. IL-10 is a pleiotropic homodimeric cytokine produced by immune system cells, as well as some tumor cells (Ekmekcioglu et al., 1999). Its immunosuppressive function includes potent inhibition of proinflammatory cytokine synthesis, including that of IFNγ, TNFα, and IL-6 (De Waal Malefyt et al., 1991). The family of IL-10like cytokines is encoded in a small 195 kb gene cluster on chromosome 1q32, and consists of a number of cellular proteins (IL-10, IL-19, IL-20, MDA-7) with structural and sequence homology to IL-10 (Kotenko et al., 2000; Gallagher et al., 2000; Blumberg et al., 2001; Dumoutier et al., 2000; Knapp et al., 2000; Jiang et al., 1995a; Jiang et al., 1996).

A recently discovered putative member of the cytokine family is MDA-7. MDA-7 has been characterized as an IL-10 family member and is also known as IL-24. Chromosomal location, transcriptional regulation, murine and rat homologue expression, and putative protein structure all allude to MDA-7 being a cytokine (Knapp et al., 2000; Schaefer et al., 2000; Soo et al., 1999; Zhang et al., 2000). Similar to GM-CSF, TNFα, and IFNγ transcripts, all of which contain AU-rich elements in their 3'UTR targeting mRNA for rapid degradation, MDA-7 has three AREs in its 3'UTR[17]. Mda-7 mRNA has been identified in human PBMC (Ekmekcioglu, et al., 2001), and although no cytokine function of human MDA-7 protein has been previously reported, MDA-7 has been designated as IL-24 based on the gene and protein sequence characteristics (NCBI database accession XM_001405).

Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine.

Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta.-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

As will be understood by those in the art, the term "therapeutic gene" includes genomic sequences, cDNA sequences, and smaller engineered gene segments that express, or may be adapted to express, proteins, polypeptides, domains, peptides, fusion proteins, and mutants. The nucleic acid molecule encoding a therapeutic gene may comprise a contiguous nucleic acid sequence of about 5 to about 12000 or more nucleotides, nucleosides, or base pairs.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

Encompassed within the definition of "therapeutic gene" is a "biologically functional equivalent" therapeutic gene. Accordingly, sequences that have about 70% to about 99% homology of amino acids that are identical or functionally equivalent to the amino acids of the therapeutic gene will be sequences that are biologically functional equivalents provided the biological activity of the protein is maintained.

4. Selectable Markers

In certain embodiments of the invention, a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Examples of selectable and screenable markers are well known to one of skill in the art.

5. Reporters

The term "reporter," "reporter gene" or "reporter sequence" as used herein refers to any genetic sequence or encoded polypeptide sequence that is detectable and distinguishable from other genetic sequences or encoded polypeptides present in cells. Preferably, the reporter sequence encodes a protein that is readily detectable either by its presence, or by its activity that results in the generation of a detectable signal. In certain aspects, a detectable moiety may include a fluorophore, a luminophore, a microsphere, an enzyme, a polypeptide, a polynucleotide, and/or a nanosphere, all of which may be coupled to an antibody or a ligand that recognizes and/or interacts with a reporter. In various embodiments, a nucleic acid sequence of the invention comprises a reporter nucleic acid sequence or encodes a product that gives rise to a detectable polypeptide. A reporter is or encodes a reporter molecule which is capable of directly or indirectly generating a detectable signal. Generally, although not necessarily, the reporter gene encodes RNA and/or detectable protein that are not otherwise produced by the cells. Many reporter genes have been described, and some are commercially available for the study of gene regulation. See, for example, Alam and Cook, 1990, Anal. Biochem. 188:245-254, the disclosure of which is incorporated herein by reference. Signals that may be detected include, but are not limited to color, fluorescence, luminescence, isotopic or radioisotopic signals, cell surface tags, cell viability, relief of a cell nutritional requirement, cell growth and drug resistance. Reporter sequences include, but are not limited to, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, G-protein coupled receptors, somatostatin receptors, CD2, CD4, CD8, the influenza hemagglutinin protein, symporters (such as NIS) and others well known in the art, to which high affinity antibodies or ligands directed thereto exist or can be produced by conventional means, and fusion proteins comprising a membrane bound protein appropriately fused to an antigen tag domain from, among others, hemagglutinin or Myc.

In certain embodiments, the reporter amino acid sequence is a G-protein coupled receptor amino acid sequence. Exemplary G-protein coupled receptors include acetylcholine receptor: M1, M2, M3, M4, or M5; adenosine receptor: A1; A2A; A2B; or A3; adrenoceptors: alpha1A, alpha1B, alpha1D, alpha2A, alpha2B, alpha2C beta1, beta2, or beta3; angiotensin receptors: AT1, or AT2; bombesin receptors: BB1, BB2, or BB3; bradykinin receptors: B1, B2, calcitonin, Ainilin, CGRP, or adrenomedullin receptors; cannabinoid receptors: CB1, or CB2; chemokine receptors: CCR1, CCR2, CCR3, CCR4, CCR5, CCR6, CCR7, CCR8, CCR9, CCR10, CXCR1, CXCR2, CXCR3, CXCR4, CXCR5, CX3CR1, or XCR1; chemotactic receptors : C3a, C5a, or fMLP; cholecystokinin and gastrin receptors: CCK1, or CCK2; corticotropin-releasing factor receptors: CRF1, or CRF2; dopamine receptors: D1, D2, D3, D4, or D5; endothelin receptors: ET(A) or ET(B); galanin receptors: GAL1, GAL2, or GAL3; glutamate receptors: mgl1, mgl2, mgl3, mgl4, mgl5, mgl6, mgl7, or mgl8; glycoprotein hormone receptors: FSH, LSH, or TSH; histamine receptors: H1, H2, H3, or H4; 5-HT receptors: 5-HT1A, 5-HT1B, 5-HT1D, 5-HT1B, 5-HT1F, 5HT2A, 5-HT2F, 5-HT2C, 5-HT3, 5-HT4, 5-HT5A, 5-HT5B, 5-HT6, or 5-HT7; leukotriene receptors: BLT, CysLT1, or CysLT2; lysophospholipid receptors: edg1, edg2, edg3, or edg4; melanocorlin receptors: MC1; MC2; MC3; MC4, or MC5; melatonin receptors: MT1, MT2, or MT3; neuropeptide Y receptors: Y1, Y2, Y4, Y5, or Y6; neurotension receptors: NTS1, or NTS2; opioids: DOP, KOP, MOP, or NOP; P2Y receptors: P2Y1, P2Y2, P2Y4, P2Y6, P2Y11, or P2Y12); peroxisome proliferators: PPAR-alpha, PPAR-beta, or PPAR-gamma; prostanoid receptors: DP, FP, IP, TP, EP1, EP2, EP3, or EP4; protease-activated receptors: PAR1, PAR2, PAR3, or PAR4; Somatostatin receptors: SSTR1, SSTR2, SSTR2A, SSTR3, SSTR4, or SSTR5; tachykinin receptors: NK1, NK2, or NK3; thyrotropin-releasing hormone receptors: TRH1, or TRH2; urotensin-II receptor; vasoactivate intestinal peptide or pituitary adenylate cyclase activating peptide receptors: VPAC1, VPAC2, or PAC1; or vasopressin or oxytocin receptors: V1a, V1b, V2, or OT. The use of somatostatin receptors as reporters is discussed in greater detail in U.S. Patent Application Publication No. 20020173626, which is herein specifically incorporated by referenced in its entirety for this section of the specification and all other sections of the specification.

In certain embodiments, expression of the reporter nucleic acid or polypeptide confers a growth advantage and the degree of the growth advantage is controllable by varying the growth conditions of the host cell.

In other embodiments, the reporter sequence encodes a fluorescent protein. Examples of fluorescent proteins which may be used in accord with the invention include green fluorescent protein (GFP), enhanced green fluorescent protein (EGFP), Renilla Reniformis green fluorescent protein, GFP-mut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

In other embodiments, the reporter gene may encode a cell surface tag. In association with this embodiment, the method may further comprises the step of contacting the host cell with a fluorescently labeled antibody specific for the cell surface tag, thereby labeling the host cell, which may be isolated by FACS or other sorting or isolation methods.

In various embodiments, the desired level of expression of at least one of the reporter sequence is an increase, a decrease, or no change in the level of expression of the reporter sequence as compared to the basal transcription level of the reporter sequence. In a particular embodiment, the desired level of expression of one of the reporter sequences is an increase in the level of expression of the reporter sequence as compared to the basal transcription level of the reporter sequence.

In various embodiments, the reporter sequence encode unique detectable proteins which can be analyzed independently, simultaneously, or independently and simultaneously. In certain embodiments, at least one of the reporter sequence encodes a fluorescent protein. In another embodiment, the expression level of at least one of the reporter sequence may be analyzed by FACS.

In other embodiments, the host cell may be a eukaryotic cell or a prokaryotic cell. Exemplary eukaryotic cells include yeast and mammalian cells. Mammalian cells include human cells and various cells displaying a pathologic phenotype, such as cancer cells.

In certain embodiments of the present invention, the reporter is a ribozyme RNA sequence. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

6. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (Chandler et al., 1997).

7. Polyadenylation Signals

One may include a polyadenylation signal in the expression construct to effect proper polyadenylation of the transcript. The nature of the polyadenylation signal is not believed to be crucial to the successful practice of the invention, and/or any such sequence may be employed. Specific embodiments include the SV40 polyadenylation signal and/ or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

8. Termination Signals

The vectors or constructs of the present invention may comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

9. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

10. IRES

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (U.S. Pat. Nos. 5,925,565 and 5,935,819; PCT/US99/05781).

B. Methods of Imaging a Cell

Certain embodiments of the present invention pertain to methods of imaging a cell that involve contacting the cell with a composition that includes a nucleic acid comprising one or more of the novel promoters set forth herein, wherein the promoter is operatively coupled to a reporter amino acid sequence, and detecting cellular expression of the reporter sequence by measuring a signal derived from the reporter. The cell may be an isolated cell, or it may be part of a tissue, such as a tissue in a subject. In certain embodiments, the cell is a tumor cell that is comprised in a tumor in a subject with cancer.

1. Methods to Measure a Signal

The signal to be measured may be measured as part of an isolated imaging procedure, or as part of an imaging procedure using more than one imaging modality (discussed in greater detail below). For example, the imaging procedure may be CT, MRI, or PET as discussed below. In certain aspects, however, the imaging is performed intraoperatively during a surgical procedure on a subject. In certain embodiments, for example, the reporter can be used to selectively label a particular tissue type that the surgeon seeks to excise. For example, in some embodiments, the tissue to be excised is a tumor tissue, and the intraoperative imaging is imaging of the tumor tissue. The imaging that is performed intraoperatively is used to guide detection of cells to be excised. Intraoperative imaging may or may not be performed concurrently with administration of a therapeutic gene, wherein the therapeutic gene is operatively coupled to the reporter sequence.

In certain embodiments, imaging is performed concurrently with administration of a therapeutic gene to a subject. For example, in addition to being operatively coupled to a reporter amino acid sequence, the promoter may also be operatively coupled to a therapeutic gene. The therapeutic gene can be any type of therapeutic gene known to those of ordinary skill in the art. For example, the therapeutic gene may be a tumor suppressor gene, a gene that induces apoptosis, a gene encoding an enzyme, a gene encoding antibody, or a gene encoding a hormone. Any therapeutic gene known to those of ordinary skill in the art is contemplated by the methods of the present invention. Therapeutic genes are discussed in greater detail elsewhere in this specification.

Concurrent administration of a reporter amino acid sequence operatively coupled to a therapeutic gene can also be applied in measurement of the biodistribution of a gene in a subject. Thus, the methods of imaging a cell set forth herein can be applied to measure biodistribution of a therapeutic gene in a tissue, such as biodistribution of a therapeutic gene in a tumor in a subject with cancer.

Imaging of the reporter amino acid sequence can be performed by any method known to those of ordinary skill in the art. For example, the reporter may be imaged by administration of a labeled ligand to a subject, wherein the labeled ligand is directed to the reporter amino acid sequence. In other embodiments, the ligand is a radiolabeled probe, such as 111-In-octreotide. In further embodiments, the ligand is a fluorescent probe directed against the reporter amino acid sequence, or an antibody directed against the reporter amino acid sequence.

Any method known to those of ordinary skill in the art for measuring a signal derived from a reporter is contemplated for inclusion in the present invention. Exemplary methods of detecting are delineated as follows.

a. Gamma Camera Imaging

A variety of nuclear medicine techniques for imaging are known to those of ordinary skill in the art. Any of these techniques can be applied in the context of the imaging methods of the present invention to measure a signal from the reporter. For example, gamma camera imaging is contemplated as a method of imaging that can be utilized for measuring a signal derived from the reporter. One of ordinary skill in the art would be familiar with techniques for application of gamma camera imaging see, e.g., Kundra et al., 2002, herein specifically incorporated by reference). In one embodiment, measuring a signal can involve use of gamma-camera imaging of a 111-In-octreotide-SSRT2A reporter system.

b. Computerized Tomography (CT)

Computerized tomography (CT) is contemplated as an imaging modality in the context of the present invention. By taking a series of X-rays, sometimes more than a thousand, from various angles and then combining them with a computer, CT made it possible to build up a three-dimensional image of any part of the body. A computer is programmed to display two-dimensional slices from any angle and at any depth.

In CT, intravenous injection of a radiopaque contrast agent can assist in the identification and delineation of soft tissue masses when initial CT scans are not diagnostic. Similarly, contrast agents aid in assessing the vascularity of a soft tissue or bone lesion. For example, the use of contrast agents may aid the delineation of the relationship of a tumor and adjacent vascular structures.

CT contrast agents include, for example, iodinated contrast media. Examples of these agents include iothalamate, iohexol, diatrizoate, iopamidol, ethiodol, and iopanoate. Gadolinium agents have also been reported to be of use as a CT contrast agent (see, e.g., Henson et al., 2004). For example, gadopentate agents has been used as a CT contrast agent (discussed in Strunk and Schild, 2004).

In embodiments of the present invention, for example, a ligand directed against the reporter or a tag fused to the reporter can be labeled with a CT contrast agent. Performance of CT imaging can then be used to measure a signal derived from the reporter.

c. Magnetic Resonance Imaging (MRI)

Magnetic resonance imaging (MRI) is an imaging modality that is newer than CT that uses a high-strength magnet and radio-frequency signals to produce images. The most abundant molecular species in biological tissues is water. It is the quantum mechanical "spin" of the water proton nuclei that ultimately gives rise to the signal in imaging experiments. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT image, is normally displayed in two-dimensional slices.

Contrast agents used in MR imaging differ from those used in other imaging techniques. Their purpose is to aid in distinguishing between tissue components with identical signal characteristics and to shorten the relaxation times (which will produce a stronger signal on T1-weighted spin-echo MR images and a less intense signal on T2-weighted images). Examples of MRI contrast agents include gadolinium chelates, manganese chelates, chromium chelates, and iron particles.

Both CT and MRI provide anatomical information that aid in distinguishing tissue boundaries and vascular structure. Compared to CT, the disadvantages of MRI include lower patient tolerance, contraindications in pacemakers and certain other implanted metallic devices, and artifacts related to multiple causes, not the least of which is motion (Alberico et al., 2004). CT, on the other hand, is fast, well tolerated, and readily available but has lower contrast resolution than MRI and requires iodinated contrast and ionizing radiation (Alberico et al., 2004). A disadvantage of both CT and MRI is that neither imaging modality provides functional information at the cellular level. For example, neither modality provides information regarding cellular viability.

As set forth above with CT imaging, a ligand labeled with an MRI contrast agent, wherein the ligand is directed to the reporter or a tag fused to the reporter, can be measured using MRI to determine presence of a signal derived from the reporter.

d. PET and SPECT

Imaging modalities that provide information pertaining to information at the cellular level, such as cellular viability, include positron emission tomography (PET) and single-photon emission computed tomography (SPECT). In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high.

Closely related to PET is single-photon emission computed tomography, or SPECT. The major difference between the two is that instead of a positron-emitting substance, SPECT uses a radioactive tracer that emits high-energy photons. SPECT is valuable for diagnosing coronary artery disease, and already some 2.5 million SPECT heart studies are done in the United States each year.

PET radiopharmaceuticals for imaging are commonly labeled with positron-emitters such as $^{11}$C, $^{13}$N, $^{15}$O, $^{18}$F, $^{82}$Rb, $^{62}$Cu, and $^{68}$Ga. SPECT radiopharmaceuticals are commonly labeled with positron emitters such as $^{99m}$Tc, $^{201}$Tl, and $^{67}$Ga. Regarding brain imaging, PET and SPECT radiopharmaceuticals are classified according to blood-brain-barrier permeability, cerebral perfusion and metabolism receptor-binding, and antigen-antibody binding (Saha et al., 1994). The blood-brain-barrier SPECT agents, such as $^{99m}$TcO4-DTPA, $^{201}$Tl, and [$^{67}$Ga]citrate are excluded by normal brain cells, but enter into tumor cells because of altered BBB. SPECT perfusion agents such as [$^{123}$I]IMP, [$^{99m}$Tc]HMPAO, [$^{99m}$Tc]ECD are lipophilic agents, and therefore diffuse into the normal brain. Important receptor-binding SPECT radiopharmaceuticals include [$^{123}$I]QNE, [$^{123}$I]IBZM, and [$^{123}$I] iomazenil. These tracers bind to specific receptors, and are of importance in the evaluation of receptor-related diseases.

e. Optical Imaging

Optical imaging is another imaging modality that has gained widespread acceptance in particular areas of medicine. Examples include fluorescence imaging analysis, immunohistochemical imaging analysis, and chemiluminescence imaging analysis. One of ordinary skill in the art would be very familiar with these forms of imaging modalities. Additional examples include optical labeling of cellular components, and angiography such as fluorescein angiography and indocyanine green angiography. Examples of optical imaging agents include, for example, fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye.

f. Ultrasound

Another biomedical imaging modality that has gained widespread acceptance is ultrasound. Ultrasound imaging has been used noninvasively to provide realtime cross-sectional and even three-dimensional images of soft tissue structures and blood flow information in the body. High-frequency sound waves and a computer to create images of blood vessels, tissues, and organs.

Ultrasound imaging of blood flow can be limited by a number of factors such as size and depth of the blood vessel. Ultrasonic contrast agents, a relatively recent development, includes perfluorine, and perfluorine analogs, which are designed to overcome these limitations by helping to enhance grey-scale images and Doppler signals.

2. Multimodality Imaging

In some embodiments of the present invention, imaging using more than one imaging modality can be used to measure a signal derived from the reporter. Any two or more imaging modalities known to those of ordinary skill in the art can be applied in the present invention to measure a signal derived from the reporter.

The imaging modalities are performed at any time during or after administration of the composition comprising the diagnostically effective amount of the compound that comprises an oligosaccharide conjugated to two imaging moieties. For example, the imaging studies may be performed during administration of the dual imaging compound of the present invention, or at any time thereafter. In some embodiments, the first imaging modality is performed beginning concurrently with the administration of the dual imaging agent, or about 1 sec, 1 hour, 1 day, or any longer period of time following administration of the dual imaging agent, or at any time in between any of these stated times. In some embodiments of the present invention a second imaging modality may be performed concurrently with the first imaging modality, or at any time following the first imaging modality. For example, the second imaging modality may be performed about 1 sec, about 1 hour, about 1 day, or any longer period of time following completion of the first imaging modality, or at any time in between any of these stated times. One of ordinary skill in the art would be familiar with performance of the various imaging modalities contemplated by the present invention. Further, one of ordinary skill in the art would be familiar with imaging equipment and imaging techniques that make use of imaging using more than one imaging modality.

Examples include, but are not limited to, CT and MRI, CT and PET, CT and SPECT, CT and ultrasound, CT and optical imaging, and so forth.

3. Ligands

A ligand is defined herein to refer to an ion, a molecule, or a molecular group that binds to another chemical entity to form a larger complex. In the context of the present invention, the ligand is an ion, a molecule, or a molecular group that can bind to a reporter or to an amino acid sequence attached to the reporter sequence (e.g., such as a protein tag fused to the N-terminal end or C-terminal end of the reporter amino acid sequence) to form a larger complex. Any ligand known to those of ordinary skill in the art is contemplated for use as a ligand in the context of the present invention. In some embodiments of the present invention, a ligand may be contacted with the cell to be imaged. The ligand may or may not be internalized by the cell. Where a reporter has become localized to the cell surface, the ligand, in these embodiments, may bind to or associate with the reporter. Any method of binding of the ligand to the reporter is contemplated by the present invention. In certain other embodiments, a ligand may become internalized by a cell, and bind to or associate with a reporter within the cell.

The ligand may be a molecule or part of a molecule that has properties such that it is capable of generating a signal that can be detected. Any imaging modality known to those of ordinary skill in the art can be applied to image a ligand. In some embodiments, the ligand is capable of binding to a molecule or part of a molecule that can be imaged. For example, the ligand may be capable of binding to a radionuclide, and the radionuclide can be imaged using nuclear medicine techniques known to those of ordinary skill in the art. For example, the ligand may be 111-In-octreotide. In other embodiments, for example, the ligand is capable of binding a contrast agent that can be detected using imaging techniques well-known to those of ordinary skill in the art. For example, the ligand may be capable of binding to a CT contrast agent or an MRI contrast agent.

In certain embodiments of the present invention, a ligand can bind to the reporter, and the ligand in turn generates a signal that can be measured using an imaging modality known to those of ordinary skill in the art. In other embodiments, the ligand can bind to a protein tag that is fused to the reporter. Thus, for example, imaging would involve measuring a signal from the ligand, and this in turn would provide for localization of the reporter sequence within the cell or within a subject.

4. Radioimaging and Radionuclides for Use in Imaging

"Radioimaging" is defined herein to refer to any imaging that involves application of radionuclides or valent metal ions in the measurement of a signal. A variety of valent metal ions, or radionuclides, are known to be useful for radioimaging. Examples include $^{67}Ga$, $^{68}Ga$, $^{99m}Tc$, $^{111}In$, $^{123}I$, $^{125}I$, $^{131}I$, $^{169}Yb$, $^{60}Cu$, $^{61}Cu$, $^{62}Cu$, $^{201}Tl$, $^{72}A$, and $^{157}Gd$.

A number of factors must be considered for optimal radioimaging in humans. To maximize the efficiency of detection, a valent metal ion that emits gamma energy in the 100 to 200 keV range is preferred. A "gamma emitter" is herein defined as an agent that emits gamma energy of any range. One of ordinary skill in the art would be familiar with the various valent metal ions that are gamma emitters. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site. $^{99m}Tc$ is a preferred radionuclide because it emits gamma radiation at 140 keV, it has a physical half-life of 6 hours, and it is readily available on-site using a molybdenum-99/technetium-99m generator. One of ordinary skill in the art would be familiar with methods to determine optimal radioimaging in humans.

In some embodiments of the compositions of the present invention, a valent metal ion that is a therapeutic metal ion that is not a beta emitter or a gamma emitter can be bound to the ligand or reporter amino acid sequence. For example, the therapeutic metal ion may be platinum, cobalt, copper, arsenic, selenium and thallium. Compounds including these therapeutic metal ions may be applied in the methods of the present invention directed to the treatment of hyperproliferative disease, such as the treatment of cancer.

In certain embodiments of the present invention, the nucleic acid for use in the imaging methods of the present invention encodes an amino acid sequence that can be radiolabeled. Radiolabeling of the encoded reporter sequence can be direct, or it can be indirect, such as by radiolabeling of a ligand that can bind the protein tag or reporter sequence. Radiolabeled agents, compounds, and compositions provided by the present invention are provided having a suitable amount of radioactivity. For example, in forming $^{99m}Tc$ radioactive complexes, it is generally preferred to form radioactive complexes in solutions containing radioactivity at concentrations of from about 0.01 millicurie (mCi) to about 300 mCi per mL.

Once the encoded sequence is radiolabled, it can be imaged for visualizing a site, such as a tumor in a mammalian body. In accordance with this invention, the radiolabel is administered by any method known to those of ordinary skill in the art. For example, administration may be in a single unit injectable dose, administered as a radiolabeled ligand. Any of the common carriers known to those with skill in the art, such as sterile saline solution or plasma, may be utilized. Generally, a unit dose to be administered has a radioactivity of about 0.01 mCi to about 300 mCi, preferably 10 mCi to about 200 mCi. The solution to be injected at unit dosage is from about 0.01 mL to about 10 mL.

After intravenous administration of the radiolabeled reagent, imaging of the organ or tumor in vivo can take place, if desired, in hours or even longer, after the radiolabeled reagent is introduced into a patient. In most instances, a sufficient amount of the administered dose will accumulate in the area to be imaged within about 0.1 of an hour.

As set forth above, imaging may be performed using any method known to those of ordinary skill in the art. Examples include PET, SPECT, and gamma scintigraphy. In gamma scintigraphy, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

5. Methods of Delivering a Gene Concurrent with Imaging

Certain embodiments of the present invention involve the concurrent administration of a gene, wherein the gene is operatively coupled to the nucleic acid encoding the reporter amino acid sequence. For example, the gene may be a therapeutic gene. Therapeutic genes are discussed in detail elsewhere in this specification. A therapeutic gene can be administered for any purpose, such as treatment of an enzyme disorder, treatment of a hormone deficiency, or treatment of cancer.

Thus, for example, the imaging methods of the present invention can be applied to concurrently measure biodistribution of a gene, such as a therapeutic gene, following administration of the gene to a subject. Furthermore, the methods of imaging can also be concurrently applied as methods to measure response to administration of a therapeutic gene in a subject. The imaging methods set forth above can be used to localize presence of the gene within the tissues of a subject, such as location within a tumor. Thus, the imaging methods can be used to determine tumor cell viability within a tumor, and can be applied in following response to therapy following administration of a therapeutic gene.

C. Delivery Vehicles for Delivery of a Nucleic Acid into a Cell

Certain embodiments of the present invention generally pertain to compositions that include one or more of the novel promoters set forth herein and a delivery vehicle for delivery of the promoter sequence into a cell in a subject. One of ordinary skill in the art would understand use of delivery vehicles for delivery of a nucleic acid since these experimental methods are well-known in the art.

Any delivery vehicle known to those of ordinary skill in the art is contemplated as a delivery vehicle for use in the present invention. For example, the delivery vehicle may include a plasmid, a viral vector, a lipid, a prokaryotic cell, or a eukaryotic cell.

1. Viral Vectors

In some embodiments of the present invention, the delivery vehicle is a viral vector. Techniques of nucleic acid delivery into a cell using "viral vectors" are well-known in the art. A viral vector is meant to include those constructs containing viral sequences sufficient to (a) support packaging of the expression cassette and (b) to ultimately express a recombinant gene construct that has been cloned therein.

Any viral vector known to those of ordinary skill in the art is contemplated as a delivery vehicle in the present invention. For example, the viral vector may be an adenoviral vector, a baculovirus vector, a parvovirus vector, a semiliki forest virus vector, a Sindbis virus vector, a lentivirus vector, a retroviral vector, a vaccinia viral vector, an adeno-associated viral vector, or a poxviral vector.

In certain embodiments, the delivery vehicle is an adenoviral vector. Although adenovirus vectors are known to have a low capacity for integration into genomic DNA, this feature is counterbalanced by the high efficiency of gene transfer afforded by these vectors.

Adenoviruses are currently the most commonly used vector for gene transfer in clinical settings. Among the advantages of these viruses is that they are efficient at gene delivery to both nondividing an dividing cells and can be produced in large quantities. The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus et al., 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. A person of ordinary skill in the art would be familiar with experimental methods using adenoviral vectors.

The adenovirus vector may be replication defective, or at least conditionally defective, and the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus growth and manipulation is known to those of skill in the art, and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. A person of ordinary skill in the art would be familiar with well-known techniques that are available to construct a retroviral vector.

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. Nos. 5,139,941 and 4,797,368, each incorporated herein by reference.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). A person of ordinary skill in the art would be familiar with techniques available to generate vectors using AAV virus.

Herpes simplex virus (HSV) has generated considerable interest in treating nervous system disorders due to its tropism for neuronal cells, but this vector also can be exploited for other tissues given its wide host range. Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995). A person of ordinary skill in the art would be familiar with well-known techniques for use of HSV as vectors.

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

Other viral vectors may be employed as constructs in the present invention. For example, vectors derived from viruses such as poxvirus may be employed. A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997). It is contemplated in the present invention, that VEE virus may be useful in targeting dendritic cells.

A polynucleotide may be housed within a viral vector that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies. against major histocompatibility complex class I and class II antigens, they demonstrated the infection of a variety of human cells that bore those surface antigens with an ecotropic virus in vitro (Roux et al., 1989).

Oncolytic viruses are also contemplated as vectors in the present invention. Oncolytic viruses are defined herein to generally refer to viruses that kill tumor or cancer cells more often than they kill normal cells. Exemplary oncolytic viruses include adenoviruses which overexpress ADP. Overexpression of ADP may be defined as any increase in ADP expression compared to expression of ADP from viruses that express wild-type levels of ADP. These viruses are discussed in detail in U.S. Patent Application Pub. No. 20040213764, U.S. Patent Application Pub. No. 20020028785, and U.S. patent application Ser. No. 09/351,778, each of which is specifically incorporated by reference in its entirety into this section of the application and all other sections of the application.

Other viral vectors that may be employed as vectors in the present invention include those viral vectors that can be applied in vaccines, or in dual vaccine and immunotherapy applications. Viral vectors, and techniques for vaccination and immontherapy using viral vectors, are described in greater detail in PCT application WO0333029, WO0208436, WO0231168, and WO0285287, each of which is specifically incorporated by reference in its entirely for this section of the application and all other sections of this application. Additional vectors that can be applied in the techniques for vaccination and dual immunotherapy/vaccination include those oncolytic viruses set forth above.

Other viral vectors also include baculovirus vectors, parvovirus vectors, picornavirus vectors, alphavirus vectors, semiliki forest virus vectors, Sindbis virus vectors, lentivirus vectors, and retroviral vectors. Vectors derived from viruses such as poxvirus may be employed. A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997). It is contemplated in the present invention, that VEE virus may be useful in targeting dendritic cells.

2. Nonviral Vectors

Any non-viral delivery vehicle that can be applied in the transfer of a nucleic acid, such as a promoter, into a cell is also contemplated by the present invention. One of ordinary skill in the art would be familiar with the range of nonviral delivery vehicles that are available.

In certain embodiments, the nucleic acid to be delivered into a cell is comprised in a plasmid. One of ordinary skill in the art would be familiar with plasmids as agents that can be used to delivery a nucleic acid sequence of interest into a cell.

In certain other embodiments, the nucleic acid to be delivered into a cell is comprised in a cell. Any cell type known to those of ordinary skill in the art is contemplated as a delivery for nucleic acids. For example, the cell may be a procaryotic cell or a eukaryotic cell.

Any method for delivery of the nucleic acid into a cell is contemplated by the present invention. These methods include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), polycations (Bousssif et al., 1995) and receptor-mediated transfection (Wu and Wu, 1987; Wu and Wu, 1988). Some of these techniques may be successfully adapted for in vivo or ex vivo use. A person of ordinary skill in the art would be familiar with the techniques pertaining to use of nonviral vectors, and would understand that other types of nonviral vectors than those disclosed herein are contemplated by the present invention.

In a further embodiment of the invention, the expression cassette may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL). One of ordinary skill in the art would be familiar with techniques utilizing liposomes and lipid formulations.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use subcutaneous, intradermal, intratumoral, or intracranial injection to avoid the toxicity and stability problems associated with cationic lipids in the circulation. The interaction of liposomes and plasma proteins is responsible for the disparity between the efficiency of in vitro (Felgner et al., 1987) and in vivo gene transfer (Zhu et al., 1993; Solodin et al., 1995; Thierry et al., 1995; Tsukamoto et al., 1995; Aksentijevich et al., 1996).

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Liposomal encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

In certain embodiments of the present invention, the delivery vehicle comprises DOTAP:cholesterol nanoparticles. DOTAP:cholesterol nanoparticles are discussed in greater detail in Templeton et al., 1997, herein specifically incorporated by reference.

D. Treatment and Prevention of Hyperproliferative Disease

1. Hyperproliferative Diseases

The present invention contemplates methods to prevent, inhibit, or treat a hyperproliferative disease in a subject by administration of a pharmaceutically effective amount of a composition comprising any of the promoter sequences set forth herein. Any nucleic acid sequence comprising any promoter sequence set forth herein that can be applied or administered to a subject for the purpose of preventing, inhibiting, or treating a disease is contemplated for inclusion in the pharmaceutical compositions set forth herein.

The disease can be any disease that can affect a subject that would be amenable to therapy or prevention through administration of a nucleic acid sequence to the subject. For example, the disease may be a hyperproliferative disease. A hyperproliferative disease is a disease associated with the abnormal growth or multiplication of cells. The hyperproliferative disease may be a disease that manifests as lesions in a subject. Exemplary hyperproliferative lesions include pre-malignant lesions, cancer, and tumors.

Other examples of diseases to be treated include infectious diseases and inflammatory diseases, such as autoimmune diseases. The methods and compositions of the present invention can be applied to deliver an antigen that can be applied in immune therapy or immune prophylaxis of a disease. One of ordinary skill in the art would be familiar with the many disease entities that would be amenable to prevention or treatment using the pharmaceutical compositions and methods set forth herein.

2. Growth Inhibition Defined

Certain embodiments of the methods set forth herein pertain to methods of inhibiting the growth of a hyperproliferative disease in a subject. "Inhibiting the growth"of a hyperproliferative lesion is broadly defined and includes, for example, a slowing or halting of the growth of the lesion. Inhibiting the growth of a lesion can also include a reduction in the size of a lesion or induction of apoptosis of the cells of the lesion. Induction of apoptosis refers to a situation wherein a drug, toxin, compound, composition or biological entity bestows apoptosis, or programmed cell death, onto a cell. In a specific embodiment, the cell is a tumor cell. Growth of a lesion can be inhibited by induction of an immune response against the cells of the lesion.

E. Pharmaceutical Compositions

Pharmaceutical compositions of the present invention comprise a therapeutically or diagnostically effective amount of a nucleic acid that includes one or more of the novel promoter sequences set forth herein. The phrases "pharmaceutical or pharmacologically acceptable" or "therapeutically effective" or "diagnostically effective" refers to molecular entities and compositions that do not produce an adverse, allergic or other untoward reaction when administered to an animal, such as, for example, a human, as appropriate. The preparation of therapeutically effective or diagnostically effective compositions will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "a composition comprising a therapeutically effective amount" or "a composition comprising a diagnostically effective amount" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the present compositions is contemplated.

The compositions of the present invention may comprise different types of carriers depending on whether it is to be administered in solid, liquid or aerosol form, and whether it need to be sterile for such routes of administration as injection. The dual imaging agents and dual therapeutic agents of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art.

The actual required amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a dual imaging agent or a dual therapeutic agent. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight to about 1000 mg/kg/body weight or any amount within this range, or any amount greater than 1000 mg/kg/body weight per administration.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The compositions of the present invention may be formulated in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the radiolabeled ethylenedicysteine derivative in the required amount of the appropriate solvent with various amounts of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

F. Cells and Cell Types

Certain embodiments of the present invention generally pertain to methods of delivering a gene into a cell, involving preparing a composition comprising a gene operatively coupled to one of the novel promoters set forth herein, and contacting the composition with the cell, wherein the contacting results in delivery of the gene into the cell. Other aspects of the present invention generally pertain to methods of imaging a cell that involve contacting the cell with a composition comprising one or more of the novel promoters set forth herein, wherein the promoter is operatively coupled to a reporter amino acid sequence, and detecting cellular expression of the reporter sequence by measuring a signal derived from the reporter.

Any cell type known to those of ordinary skill in the art is contemplated as a cell for inclusion in the methods of the present invention. For example, the cell can be a normal healthy cell. Alternatively, the cell can be a diseased cell. For example, the disease may be a hyperproliferative disease, such as cancer. The cell may be of any tissue type. For example, the cell may be a breast cancer cell, a lung cancer cell, a prostate cancer cell, an ovarian cancer cell, a brain cancer cell, a liver cancer cell, a cervical cancer cell, a colon cancer cell, a renal cancer cell, a skin cancer cell, a head and neck cancer cell, a bone cancer cell, an esophageal cancer cell, a bladder cancer cell, a uterine cancer cell, a lymphatic cancer cell, a stomach cancer cell, a pancreatic cancer cell, a testicular cancer cell, a lymphoma cell, or a leukemic cell.

G. Secondary Anti-Cancer Therapy

It is an aspect of this invention that the claimed methods for treating a hyperproliferative disease can be used in combination with another agent or therapy method, preferably another cancer treatment. Treatment with the claimed dual therapeutic agent may precede or follow the other therapy method by intervals ranging from minutes to weeks. In embodiments where another agent is administered, one would generally ensure that a significant period of time did not expire between the time of each delivery, such that the agents would still be able to exert an advantageously combined effect on the cell. For example, it is contemplated that one may administer two, three, four or more doses of one agent substantially simultaneously (i.e., within less than about a minute) with the dual therapeutic agents of the present invention. In other aspects, a therapeutic agent or method may be administered within about 1 minute to about 48 hours or more prior to and/or after administering a dual therapeutic agent or agents of the present invention, or prior to and/or after any amount of time not set forth herein. In certain other embodiments, a dual therapeutic agent of the present invention may be administered within of from about 1 day to about 21 days prior to and/or after administering another therapeutic modality, such as surgery or gene therapy. In some situations, it may be desirable to extend the time period for treatment significantly, however, where several weeks (e.g., about 1 to 8 weeks or more) lapse between the respective administrations.

Various combinations may be employed, the claimed agent for dual chemotherapy and radiation therapy is derivative is "A" and the secondary agent, which can be any other therapeutic agent or method, is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of the dual therapeutic agents of the present invention to a patient will follow general protocols for the administration of chemotherapeutics, taking into account the toxicity, if any, of these agents. It is expected that the treatment cycles would be repeated as necessary. It also is contemplated that various standard therapies, as well as surgical intervention, may be applied in combination with the described arsenical agent. These therapies include but are not limited to additional chemotherapy, additional radiotherapy, immunotherapy, gene therapy and surgery.

a. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5fluorouracil, vincristin, vinblastin and methotrexate, or any analog or derivative variant of the foregoing.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

d. Genes

In yet another embodiment, the secondary treatment is a second gene therapy in which a therapeutic polynucleotide is administered before, after, or at the same time as the nucleic acid composition of the present invention. Delivery of the dual therapeutic agent in conjunction with a vector encoding a gene product will have a combined anti-hyperproliferative effect on target tissues.

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

H. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A Novel hTERT-mini-CMV (hTMC) Promoter-Mediated Tumor-Selective and High-Efficient Expression of Reporter and Tumor Suppressor Genes for Molecular Cancer Therapy 1. Construction of hTMC Promoter.

Certain novel chimeric promoters, including the hTERT-mini-CMV (hTMC) promoter, were engineered by optimally fusing essential hTERT promoter sequence with minimal CMV promoter elements. PCR was used to amplify the 463 bp of the hTERT regulatory region and 147 bp of minimum TATA box and transcription initiation region from CMV promoter. The hybrid hTERT and CMV promoters were optimized by testing various combinations and their performance in terms of tumor-selectivity and transcription promoting strength in normal and tumor cell transfectants. Using this optimized novel hTMC promoter, both high tumor-specificity and high transgene expression were achieved in vitro and in vivo, as demonstrated here using an hTMC-EGFP reporter system in vivo.

Figure 2:
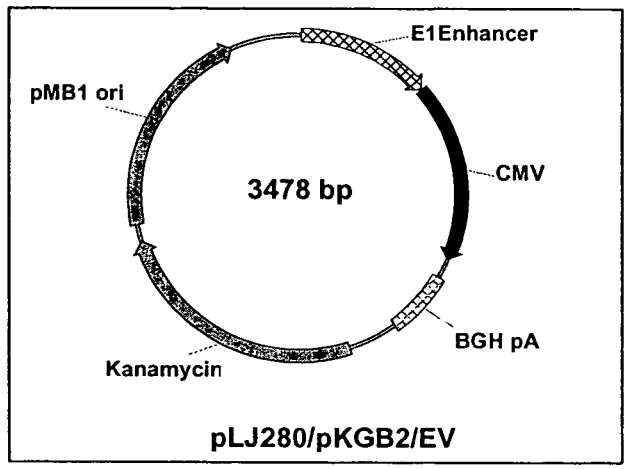
FIG. 2. Diagram of plasmid vector pLJ280/KGB2/EV.
Figure 3:
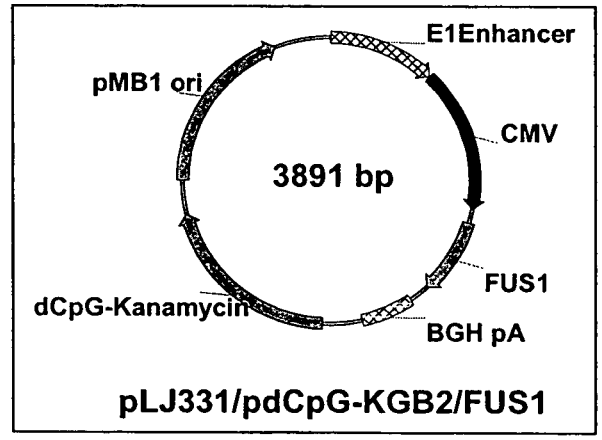
FIG. 3. Diagram of plasmid vector pLJ331/dCpG-KGB2/FUS1.
Figure 4:
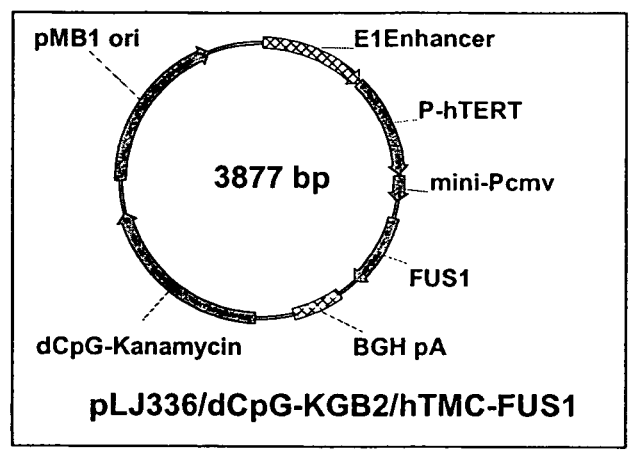
FIG. 4. Diagram of hTMC-containing plasmid vector pLJ336/dCPG-KGB2/hTMC-FUS1.
Figure 5:
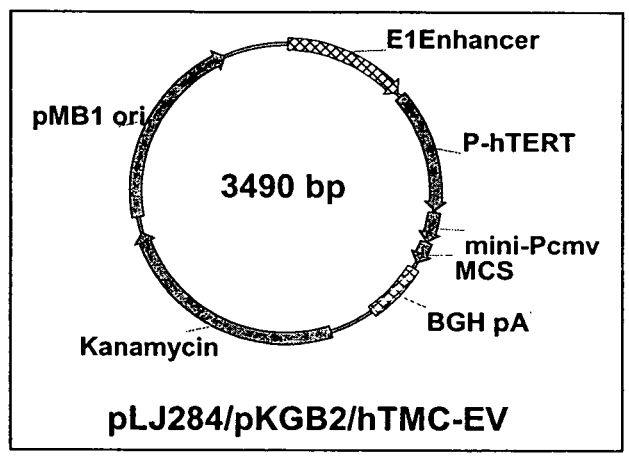
FIG. 5. Diagram of hTMC-containing plasmid vector pLJ284/pKGB2/hTMC-EV.
Figure 6:
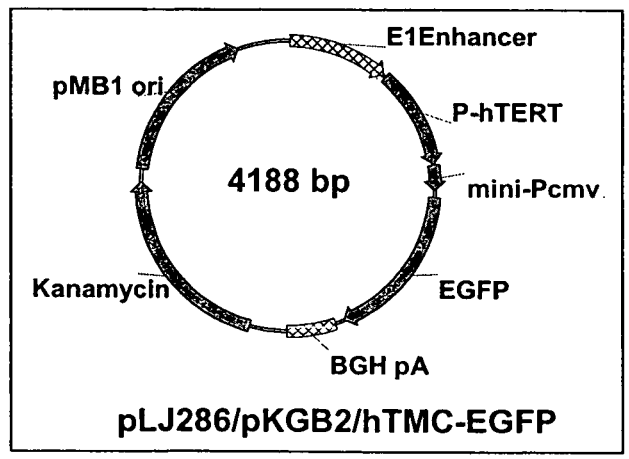
FIG. 6. Diagram of hTMC-containing plasmid vector pLJ286/pKGB2/hTMC-EGFP.
Figure 7:
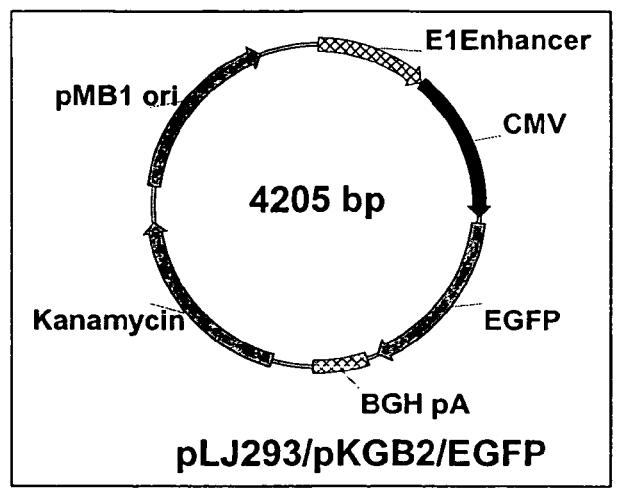
FIG. 7. Diagram of plasmid vector pLJ293/pKGB2/EGFP.
Figure 8:
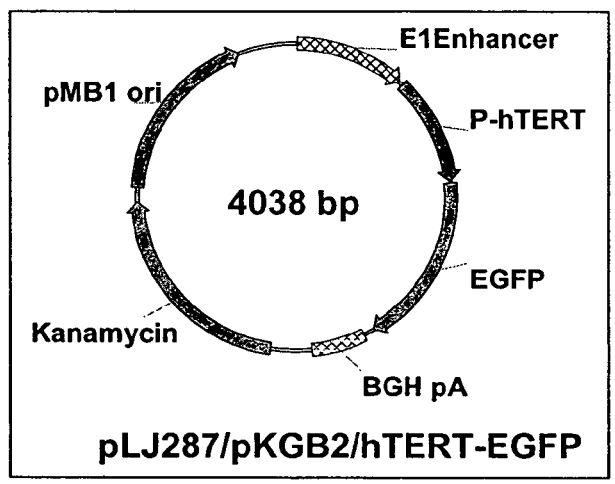
FIG. 8. Diagram of plasmid vector pLJ287/pKGB2/hTERT-EGFP.
Figure 9:
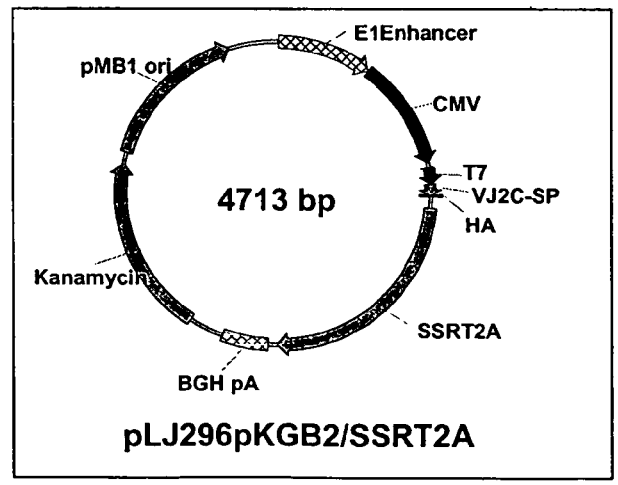
FIG. 9. Diagram of plasmid vector pLJ296/KGB2/SSRT2A.
Figure 10:
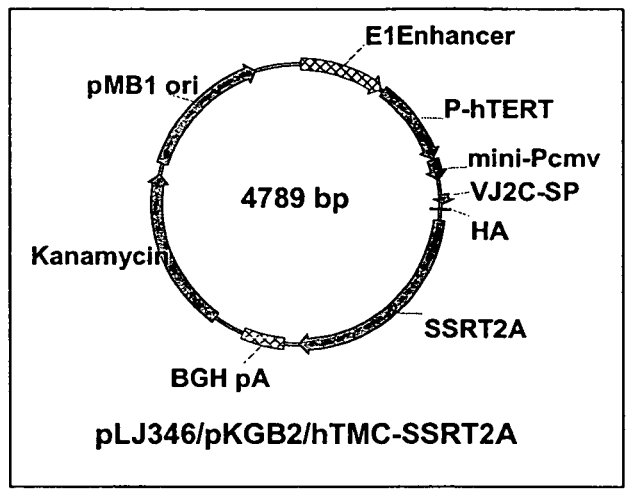
FIG. 10. Diagram of hTMC-containing plasmid vector pLJ346/KGB2/hTMC-SSRT2A.
Figure 11:
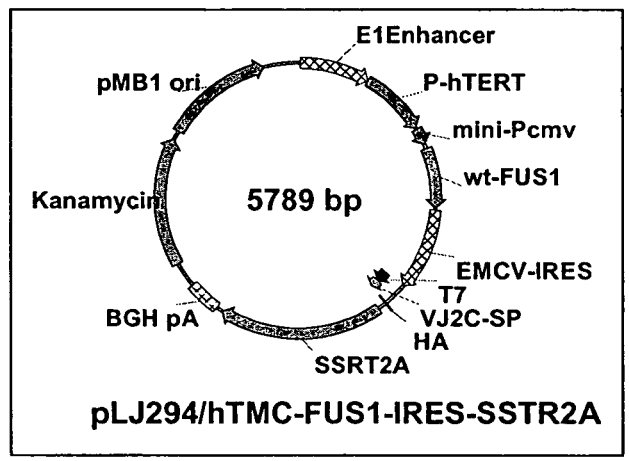
FIG. 11. Diagram of hTMC-containing plasmid vector pLJ294/hTMC-FUS1IRES-SSTR2A.
Figure 12:
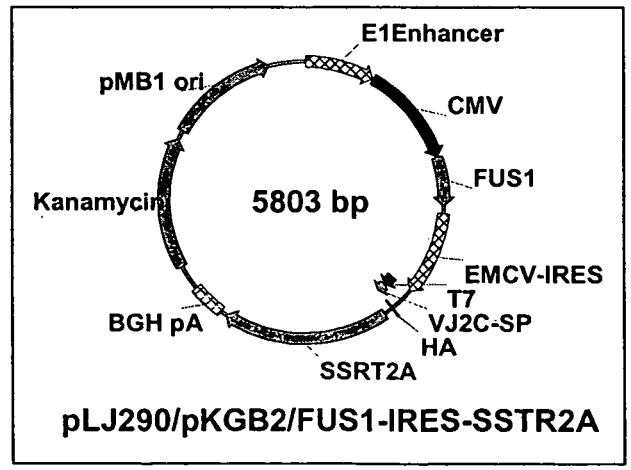
FIG. 12. Diagram of plasmid vector pLJ290/pKGB2/FUS1IRES-SSTR2A.
Figure 13:
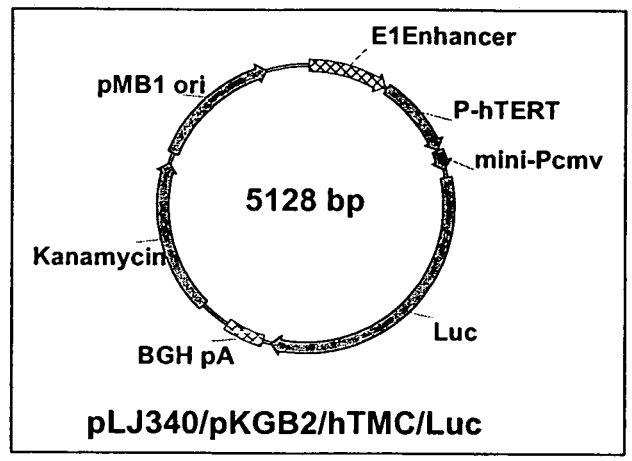
FIG. 13. Diagram of plasmid vector pLJ340/pKGB2/hTMC-Luc.
Figure 14:
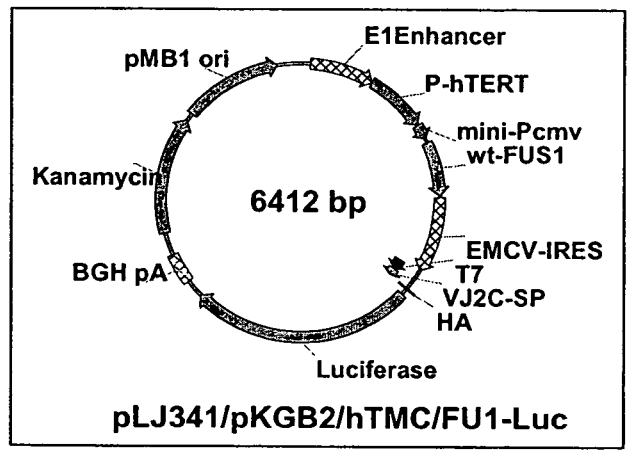
FIG. 14. Diagram of plasmid vector pLJ341/pKGB2/hTMC/FU1IRES-Luc.

2. Construction of hTMC-containing Plasmid Vectors a. pLJ143/KGB2/FUS1. This pLJ143/KGB2/FUS1 plasmid vector (FIG. 1) consists of a mammalian gene-expression cassette driven by a CMV minimum promoter with an E1 enhancer at the 3' end and a BGH-poly A signal sequence at the 5' end to ensure the efficient expression of the transgene in vivo. The kanamycin-resistance gene was chosen as the selectable marker to avoid development of antibiotic-resistance in patients. A minimum pMB1 origin of replication (ori) sequence is used to drive high-copy replication and production of the plasmid in the bacterial host strain DH5a. The plasmid backbone is minimal to ensure a higher yield of plasmid DNA production and a higher concentration of recombinant plasmid DNA per plasmid DNA preparation. The DNA sequence of the pLJ143/KGB2/FUS1 vector has been confirmed by automatic DNA sequencing and has been approved for a Phase I clinic trial (Human Gene Transfer Protocol #0201-513) by FDA. This plasmid is used as the backbone for the construction of a serial of hTMC-containing plasmid vectors for tumor-selectively expressing reporter genes and tumor suppressor genes for molecular cancer therapy and non-invasive imaging in pre-clinical and clinical applications.

b. pLJ280/KGB2/EV. The pLJ280/KGB2/EV plasmid vector (FIG. 2) is an empty (EV) plasmid vector originated from the pLJ143/KGB2/FUS1 vector, which contains all original sequence elements except the FUS1 gene insert. The 413 bp FUS1 fragment in the pLJ143 plasmid vector was removed by restriction digest with Pst I and the remaining plasmid sequence was religated to form the empty vector.

c. pLJ331/dCpG-KGB2/FUS1. The pLJ331/dCpG-KGB2/FUS1 vector (FIG. 3) contains the same plasmid DNA backbone, except the Kanamycin resistant gene has been replaced by a synthetic Kanamycin gene in which the 99 condon usage (G or C) have been altered to (A or T). This synthetic Kanamycin gene allows to completely diminish the potential CpG islands formed in the original DNA sequence but still remain the ability to use Kanamycin antibiotics to select the recombinant plasmid vectors in bacterial culture. The de-CpG'ed plasmid assumed to be less immunogenic in vivo and, thus, less toxic in pre-clinical and clinical applications by a systemic administration of the plasmid:DOTAP:cholesterol nanoparticles.

d. pLJ336/dCPG-KGB2/hTMC-FUS1 The pLJ331/dCpG-KGB2/hTMC-FUS1 vector (FIG. 4) is derived from pLJ331, in which the conventional CMV promoter is replaced by the hTMC promoter. This vector allows tumor-selective and high-efficient expression of the novel 3p21.3 tumor suppressor gene FUS1 for molecular cancer therapy in pre-clinical models and in clinical trials.

e. pLJ284/pKGB2/hTMC-EV. The pLJ284/pKGB2/hTMC-EV plasmid vector (FIG. 5) is derived from pLJ280, in which the CMV promoter is replaced by the hTMC promoter. This vector is used as a negative control in vitro and in vivo.

f. pLJ286/pKGB2/hTMC-EGFP. The pLJ286/pKGB2/hTMC-EGFP plasmid vector (FIG. 6) contains the hTMC promoter driving eukaryotical green fluorescence protein (EGFP) expression cassette. This EGFP is used as a reporter gene for evaluating the hTMC promoter-driving tumor-selective expression of EGFP, vector transfection efficiency, and biodistribution of EGFP by either fluorescence imaging analysis or by immunohistochimical analysis using anti-EGFP antibodies in cell lysates and tissue sections in vitro and in vivo.

g. pLJ293/pKGB2/EGFP. The pLJ293/pKGB2/EGFP plasmid vector (FIG. 7) contains the original non-selective CMV promoter is used as a control vector for comparison of the tumor-selective expression of EGFP with the hTMC-EGFP vector in vitro and in vivo.

h. pLJ287/pKGB2/hTERT-EGFP. The pLJ287/pKGB2/hTERT-EGFP plasmid vector (FIG. 8) contains the original hTERT promoter (with a very week transcription promoting strength but tumor-selective expression in mammalian cells) is used as a control vector for comparison of the high-efficient expression of EGFP with the hTERT-mini-CMV hybride, hTMC-EGFP vector in vitro and in vivo.

i. pLJ296/KGB2/SSRT2A. The pLJ296/KGB2/SSRT2A plasmid vector (FIG. 9) has exactly the same DNA backbone sequence as pLJ143, except a 413 bp fragment containing the transgene FUS1 in the pLJ143 plasmid vector was replaced by a SSRT2A cDNA insert (1110 bp) plus an additional DNA fragment (224 bp) containing a T7 promoter sequence, VJ2C-SP, and HA N-terminal fusion tag, which are necessary for the efficient expression of SSRT2A and detection. This vector can be used as a vector for non-invasive molecular imaging by gamma-camera imaging (GCI) with $^{111}$In-Octreotide for the whole body imaging in animal models and human clinic trial.

j. pLJ346/KGB2/hTMC-SSRT2A. The pLJ346/KGB2/hTMC-SSRT2A plasmid vector (FIG. 10) is derived from pLJ296, in which the CMV promoter is replaced with hTMC promoter for driving tumor-specific expression of SSRT2A reporter gene in vivo. This vector will allows tumor-specific imaging of the SSRT2A and significantly reduce background of in vivo images by GCI.

k. pLJ294/hTMC-FUS1IRES-SSRT2A. To overcome the limitations of the hTERT promoter and augment the transgene expression and to enhance the tumor-specific imaging of transgene expression in vivo by gamma-camera imaging with $^{111}$In-Octreotide-SSRT2A system, a novel plasmid vector, pLJ294/hTMC-SSRT2A-IRES-FUS1 vector (FIG. 11), has been developed in which the hTMC promoter will selectively drive a high level of gene expression only in the tumor cells, while the IRES elements will enable a simultaneous expression of two individual genes, the reporter SSRT2A and the therapeutic gene FUS1 with an equal level, which thus allows measurement of therapeutic FUS1 gene expression in vivo with the reporter SSTRT2A gene without interfering the normal function of FUS1 and the quantitation of expression. This vector will allow for the non-invasive monitoring of the biodistribution of cancer therapeutic genes such as FUS1, expression and clearance of transgenes, and the therapeutic efficacy in a tumor by systemic administration of the recombinant plasmid DNA:DOTAP:Cholesterol nanoparticles by GCI with the $^{111}$In-Octreotide-SSRT2A reporter system in pre-clinical and clinical trials.

l. pLJ290/pKGB2/FUS1IRES-SSTR2A. The pLJ290/KGB2/SSRT2A plasmid vector (FIG. 12) contains a similar plasmid DNA backbone and FUS1IRES-SSTR2A components, except the promoter is conventional CMV and not the hTMC promoter, as in the pLJ294 vector. This vector can be used as a control vector for comparison with the hTMC-containing pLJ294 vector in vivo.

m. pLJ340/pKGB2/hTMC-Luc. The pLJ340/pKGB2/hTMC-Luc plasmid vector (FIG. 13) contains the hTMC-promoter-driving fire fly Luciferase (Luc) expression cassette. This novel vector allows use of Luc as a convenient reporter to perform non-invasive imaging for monitoring tumor-specific trangene expression and biodistribution by a chemi-luminance camera in small animal models.

n. pLJ341/pKGB2/hTMC/FU1IRES-Luc. The pLJ341/pKGB2/hTMC/FU1IRES-Luc vector (FIG. 14) is derived from pLJ294/hTMC-FUS1IRES-SSTR2A, in which the SSTR2A reporter gene is replaced by Luc reporter gene. The hTMC promoter will selectively drive a high level of gene expression only in the tumor cells, while the IRES elements will enable a simultaneous expression of two individual genes, the reporter Luc and the therapeutic gene FUS1 with an equal level, and thus allow for measurement of therapeutic FUS1 gene expression in vivo with the reporter Luc gene but without interfering the normal function of FUS1 and the quantitation of expression in pre-clinical models using chemi-luminance camera. This vector allows non-invasive monitoring of the biodistribution of cancer therapeutic genes such as FUS1, the expression and clearance of transgenes, and the therapeutic efficacy in a tumor by systemic administration of the recombinant plasmid DNA:DOTAP:Cholesterol nanoparticles in pre-clinical trials. This vector will not need the use of radioactive materials and will be a highly-sensitive, convenient, and safe tool for the non-invasive and tumor-specific molecular imaging of cancer therapeutic genes in pre-clinical small animal models.

3. Tumor-Specific Transgene Expression Driven by the hTMV Promoter In Vitro.

Figure 15:
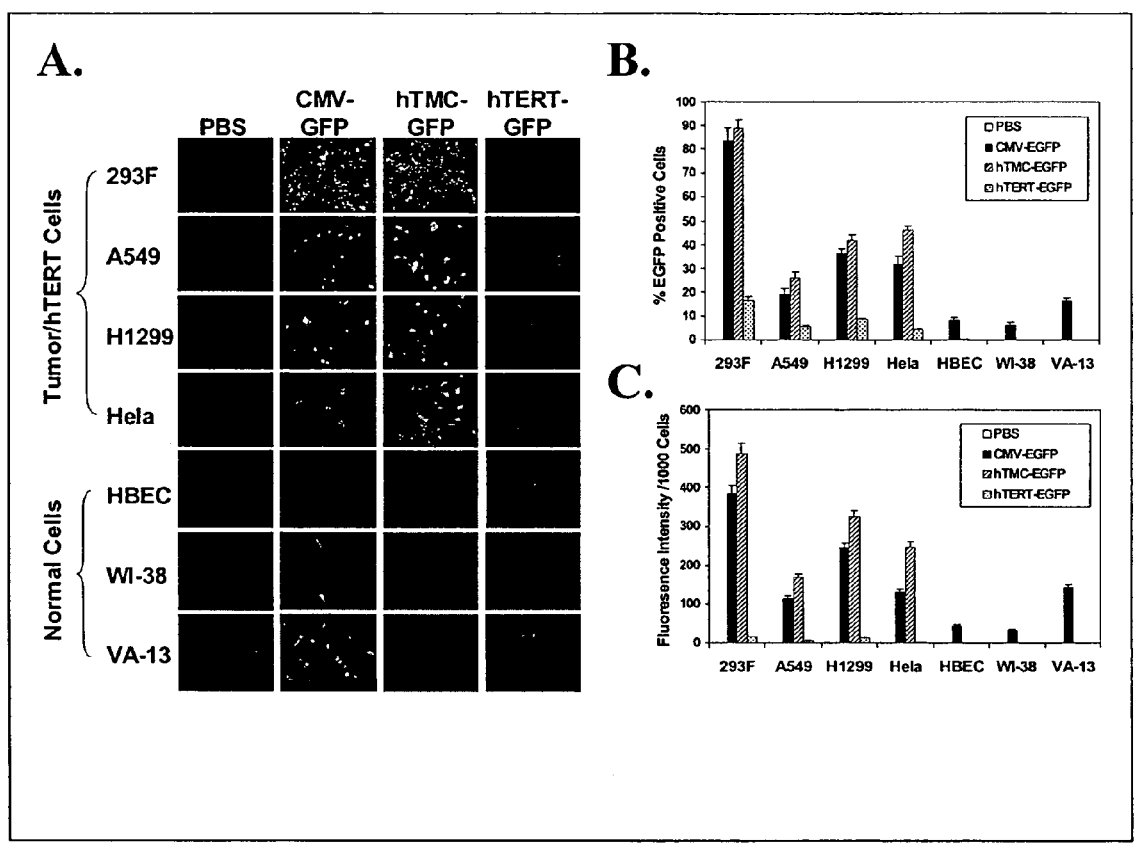
FIG. 15A, FIG. 15B, FIG. 15C. Expression of EGFP in normal and cancer cell transfectants by fluorescence imaging analysis (FIG. 15A) and quantitative analysis by FACS (FIG. 15B, the EGFP positive cells, and FIG. 15C, the total fluorescence intensity/1000 cells).

To assess the tumor-specificity and efficiency of transgene expression driven by the hTMC promoter in vitro, the plasmid pLJ286/hTMC-EGFP was used to transfect various normal and cancer cell lines using the DOTP in vitro transfecting reagent (prepared in this laboratory). The pLJ287/hTERT-EGFP and pLJ293/CMV-EGFP vectors were used as controls, and PBS treatment alone used as a mock. The activities of EGFP expression mediated by these promoters were assessed in various cultured human cancer lines cells (H1299, A549, HeLa and 293F), NHFB cells, normal fibroblast cells (WI-38) and VA-13 by analyzing the expression level of GFP 48 hours after transfection by FACS. In all cancer cell lines tested, a high level of expression of EGFP was observed in cells transfected by both the CMV- and hTMC-promoter containing vectors, but only a trace level of EGFP expression could be detected in hTERT-EGFP-transfected cancer cells (FIG. 15A, panels 293F, A549, H1299, Hela; FIG. 15B and FIG. 15C). By contrast, no expression of EGFP could be detected in normal cells HBEC, WI-38, and VA-13 cells transfected with either hTMC-EGFP or hTERT-EGFP vectors, even if expression of EGFP could still universally detected in those cells transfected by CMV-EGFP vector (FIG. 15A, panels HBEC, WI-38, VA-13, and FIG. 15B and FIG. 15C). These results indicate the tumor-specific and high efficient expression of transgene mediated by the hTERT-mini-CMV hybrid hTMC promoter.

4. Transcriptional Activity of the hTMC Promoter In Vivo.

Figure 16:
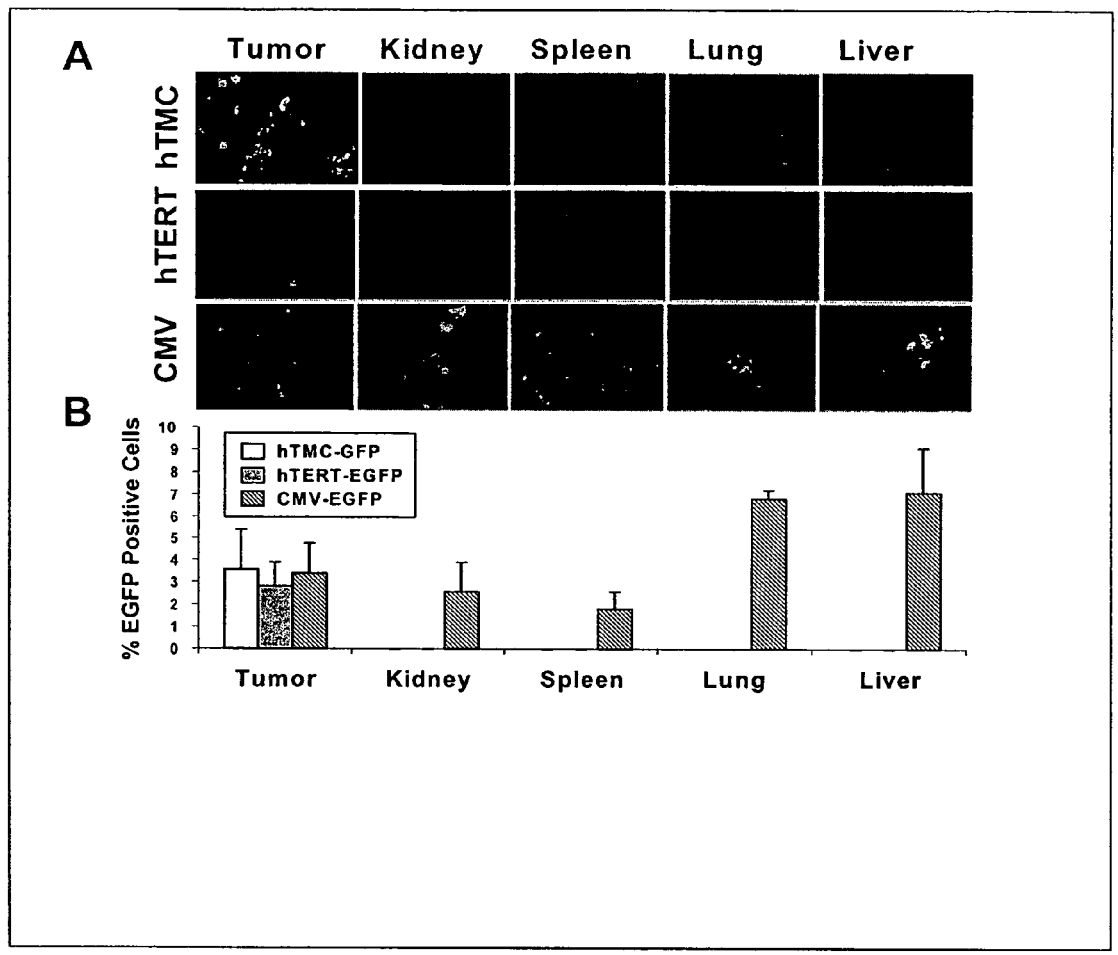
FIG. 16A, FIG. 16B. Expression of EGFP in various tissues of mice by systemic injection of EGFP-lipoplexes.

To investigate the levels of transgene expression induced by the hTMC promoter in vivo, first, human SCLC tumors were established in the lungs of mice by injection of $1 \times 10^6$ cells/mouse of human N417 SCLC cells into the thoracic space. Three weeks after tumor cell injection, solid tumors (in an average size of 2-5 mm in diameter) were established in the lung and the inner thoracic membrane of mice. The human N417 SCLC tumor-bearing animals were intravenously injected with various EGFP-lipoplexes, in which EGFP expression is driven by either original CMV and hTERT promoters or the hTMC promoter. Forty-eight hr after injection, animals were killed and organs were collected and frozen immediately. Fresh frozen tissue sections were examined under a fluorescence microscope for EGFP expression. Using this novel promoter, both high tumor-specificity and high transgene expression were achieved in vitro and in vivo, as demonstrated here using an hTMC-EGFP reporter system in vivo (FIG. 16). High levels of EGFP expression were detected only in the tumor cells in animal treated with hTMC-EGFP but not in any other normal tissues (FIG. 16A, panel hTMC). By contrast, a very weak tumor-specific EGFP expression was detected in animals treated with TERT-EGFP and an unselective expression everywhere in the tumor and normal tissues in animals treated by CMV-EGFP construct. These results indicate that a high level and tumor-specific transgene expression can be achieved by the hTMC promoter-driving gene transcription in vivo. In addition, these results indicate that this vector can be used for tumor-targeted molecular therapy for human primary and metastatic cancer by systemic administration of the recombinant hTMC-promoter containing plasmid vector, such as by DNA:DOTAP:Cholesteral nanoparticles.

5. Tumor-Targeted Non-Invasive Molecular Imaging for Evaluating Therapeutic Gene Expression by Gama-Camera Imaging with the $^{111}$In-Octreotide-SSRT2A Reporter System.

Figure 17:
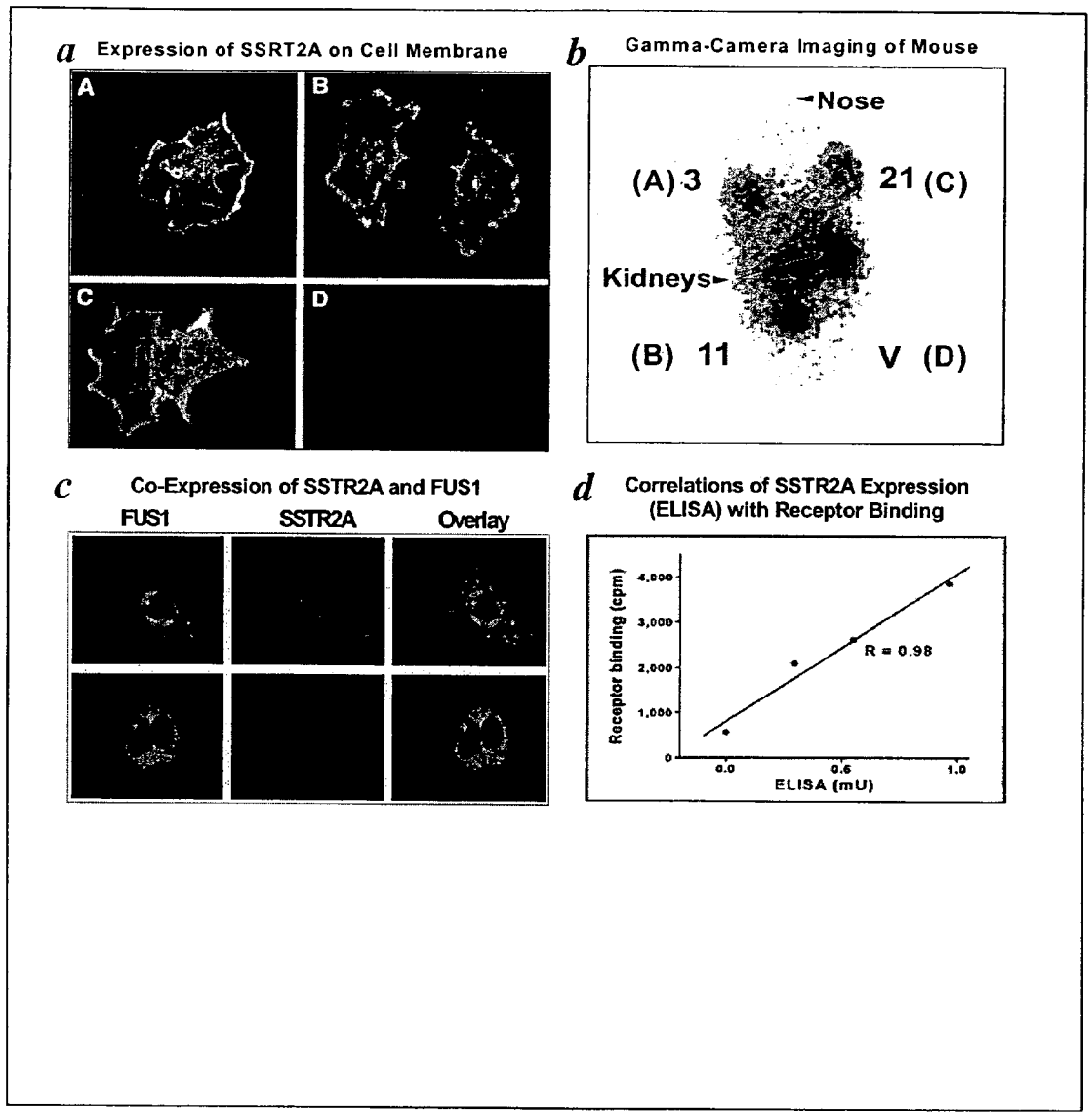
FIG. 17A, FIG. 17B, FIG. 17C, FIG. 17D.

Many in vivo molecular imaging methods for monitoring gene transfer relies on the sensitivity of gamma-camera, SPECT, or PET imaging for the detection of i.v. injected radiolabeled compounds localized to the products of transferred genes, but most of them neither directly detect the gene of interest nor exploit radiopharmaceuticals that have been FDA approval for total-body use. $^{111}$In-Octreotide is used clinically to locate tumors overexpressing primarily somatostatin receptor type 2 (SSRT2A). The cell surface membrane localization of SSRT2A products in HT1080 cells transfected with HA-SSRT2A-expressing plasmids (pHA-SSTA2A) has been successfully detected by immunoflourescence analysis with an anti-HA antibody. Mice bearing HT1080 tumors produced by pHA-SSTR2A-transfectants were injected with $^{111}$In-octreotide for biodistribution and imaging studies by gamma-camera (FIG. 17B). SSTR2A expression was also shown to be significantly correlated with both the receptor binding and $^{111}$In-octreotide radiotracer uptake by tumors (FIG. 17C). This approach demonstrated the clinical feasibility because the detected gene transfer in tumor-bearing animals with $^{111}$In-octreotide was at doses similar to those already used in humans, and also showed that it may be possible to monitor transfer of a gene of interest directly and noninvasively.

To overcome the limitations of the hTERT promoter and augment the transgene expression and to enhance the tumor-specific imaging of transgene expression in vivo by gamma-camera imaging with $^{111}$In-Octreotide-SSRT2A system, a novel plasmid vector, pLJ294/hTMC-SSRT2A-IRES-FUS1 vector, will be selectively driven by the hTMC promoter to provide for a high level of gene expression only in the tumor cells, while the IRES elements will enable a simultaneous expression of two individual genes, the reporter SSRT2A and the therapeutic gene FUS1 with an equal level. This will allow for a measurement of therapeutic FUS1 gene expression in vivo with the reporter SSTRT2A gene without interfering with the normal function of FUS1 and the quantitation of expression. The co-expression and distinguished subcellular localizations of both the SSTR2A gene (FIG. 17C, Green, cell surface membrane) and FUS1 gene (FIG. 17C and FIG. 17D, Red, mitochondria, ER, and peril-nuclear membrane locations) are clearly demonstrated by immunoflorescence imaging analysis (FIG. 17D). These novel therapeutic vectors combined with noninvasive and sensitive gamma-camera imaging with the radio-pharmaceutical $^{111}$In-octreotide will allow for efficient monitoring of the distribution, clearance, expression, and efficacy of SSTR2A-FUS1-lipoplex-mediated gene transfer in mice.

Figure 18:
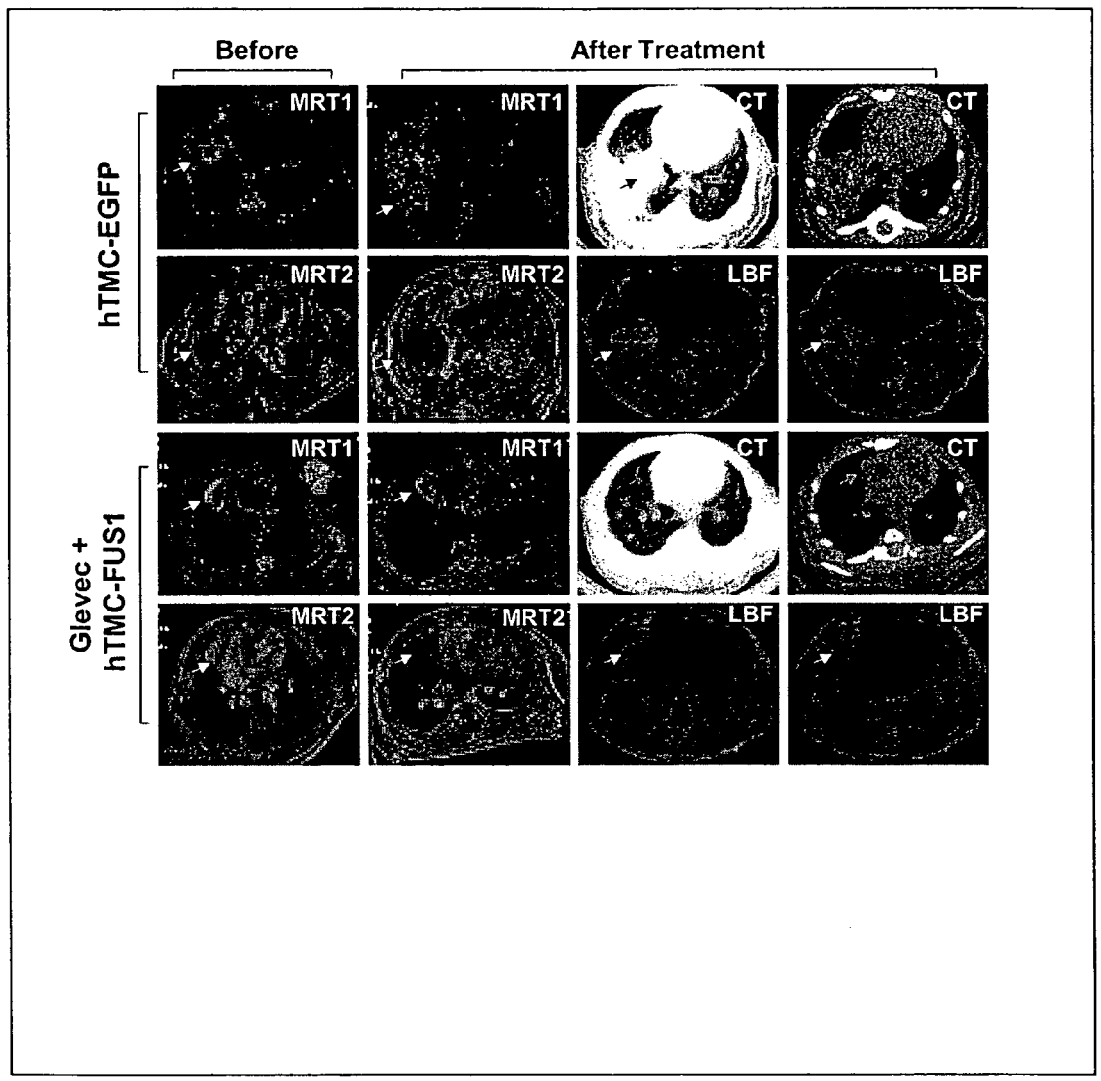
FIG. 18. MRI, CT, and Lung Block Face (LBF) imaging analysis of N417 SCLC tumor-bearing mice before and after treatment by systemic administration of hTMC-EGFP- or hTMC-FUS1 nanoparticles+Glevec via tail vein injections. Fourteen days after inoculation of N417 tumor cells by intrathoracic injection, animals were screened for tumor development by MRI (before). Two weeks after the treatment, animals were imaged by either MR or CT, then killed and whole animals were frozen immediately and block face sections were prepared and imaged intact to match the in vivo MRI and CT images.

6. Inhibition of SCLC Tumor Growth by Tumor-Targeted Molecular Therapy with Systemic Administration of phTMC-FUS1 DNA DOTAP:Cholesterol Nanoparticles and a Non-Invasive Magnetic Resonance Imaging (MRI) in Nude Mice The noninvasive approach to detection and the capabilities to obtain volumetric quantitative information and to differentiate the image intensity between tissues on the basis of variations in the local environment of water make magnetic resonance imaging (MRI) a powerful tool for a broad range of experimental cancer studies. To evaluate the efficacy of tumor-targeted molecular therapy on human lung primary and metastases cancers by systemic administration of phTMC-FUS1 DNA:DOTAP:Cholesterol nanoparticles and to non-invasively monitor the hTMC-mediated FUS1 gene expression and anti-tumor effects in vivo, an experiment was conducted to characterize the appearance of tumors using various MR parameters and to monitor tumor growth and the therapeutic effect of systemic treatment with hTMC-FUS1 nanoparticle in nude mice bearing human SCLC tumor xenografts in the intra-thoracic space and lung (FIG. 18). The nude mice were inoculated with human N417 SCLC cells by direct injection of tumor cells ($1 \times 10^6$ in 100 PBS) into thoracic space. Solid tumor xenografts were usually established within 10-15 days in the lung or metastasized to the bone or brain. MRI was performed before and after treatment by systemic administration of DOTAP:cholesterol complexed phTMC-FUS1 plasmid DNA (hTMC-FUS1 nanoparticles) via tail vein injection. About two weeks after the tumor cell inoculation and before the treatment, MRI analysis was performed, which clearly detected the presence of tumors in the lung (a, b, i, and j of FIG. 18, indicated by arrows). These preliminary results also clearly show the advantage of using MRI to follow the tumor growth and therapeutic efficacy. The tumors in the animals treated with control hTMC-EGFP nanoparticles continued to grow, as indicated by the increased tumor volume detected by MRI (c and d of FIG. 18) compared to those before treatment (a and b of FIG. 18), but tumor growth was significantly suppressed by treatment with hTMC-FUS1 nanoparticles (FIG. 18, k and l versus FIG. 18, i and j). MR images were also validated histologically with intact images from lung block-face (LBF) sections of frozen whole mouse that were killed immediately after MRI analysis (FIG. 18, g, h, o, and p). The tumor location and size were perfectly matched in both MRI and LBF images. In these experiments, the MRIs were compared with those images generated by CT scanning (FIG. 18, e, f, m, and n) in the same animals. Although tumors could be detected in some of the animals, neither the boundary of tumor with the adjacent normal tissue nor the volume of the tumor could be distinguished and measured by CT. These data show the accessibility and advantage of using noninvasive MRI in tumor screening, detection, quantification, and evaluation of therapeutic efficacy of hTMC-mediated anti-tumor genes in small animal models and in clinical practice.

Materials and Methods

Figure 19:
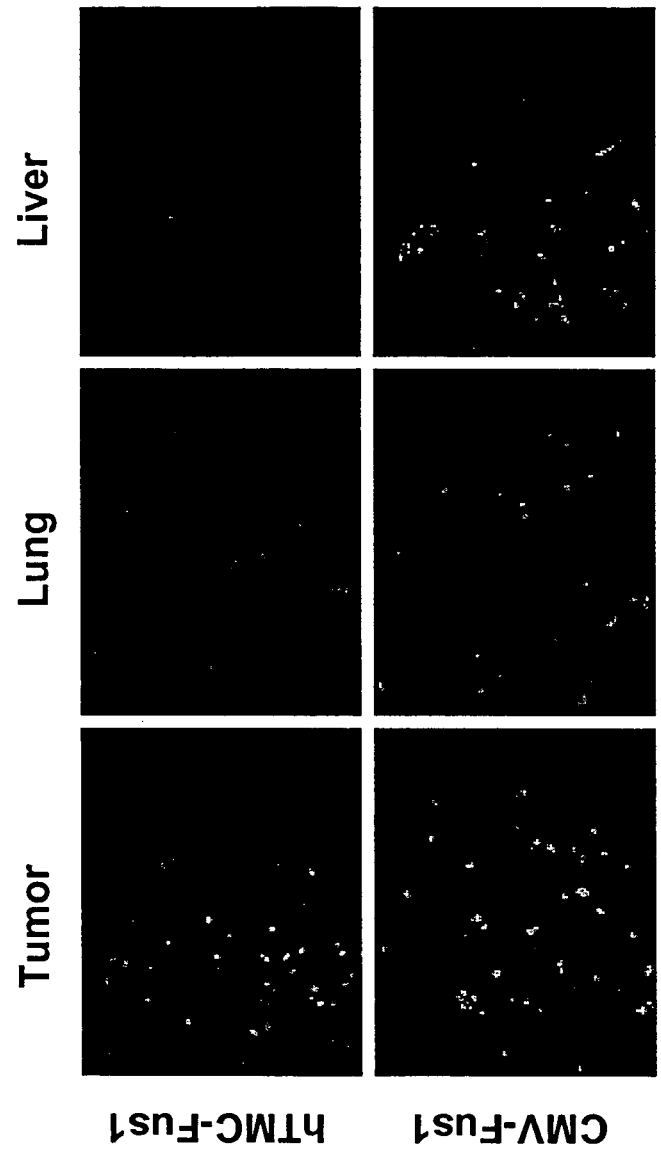
FIG. 19. Induction of apoptosis in hTMC- or CMV-FUS1 nanoparticle treated mice by in situ cell death analysis with TUNEL-reaction.

1. Cell Lines and Cell Culture. Human NSCLC cell lines NCI-H1299 and A549, the SCLC cell line N417, and cervical cell line Hela, immortal kidney cell 293F were originally obtained from American Type Culture Collection and maintained in our laboratory (M.D. Anderson Cancer Center). The normal human bronchial epithelial cell lines, HBEC, normal lung fibroblast cell lines WI-38 and VA-13, were purchased from Clonetics (Clonetics Inc., Walkersville, Md.), and cultured in media recommended by the manufacturer and according to the manufacture's instruction. All cells were cultured in a humidified atmosphere containing 5% $CO_2$ at 37° C.
2. Transfection and Analysis of in Vitro Gene Expression. FuGene 6 Reagent (Roche Inc.,) or DOTAP (produced in our laboratory) were used for in vitro transfection with plasmid vectors. PBS was used as a mock transfection. All the transfection efficiencies were detected by the percentage of reporter EGFP expression after 48 hours of transfection. In brief, cells were plated 1 day prior to promoter transfection in 6well plates, with 60-80% confluent at the time of transfection. After 48 hours of transfection, both floating and adherent cells were harvested by trypsinization, washed by PBS, and the percentages of EGFP were quantified by FACS analysis.
3. Animal Experiments. Female Nu/Nu mice, 4-6 weeks of age, were obtained from Charles River (Cambridge, Mass.). All animals were maintained and all animal experiments were conducted under institutional guidelines established for the Animal Core Facility at M.D. Anderson Cancer Center. Mice were injected with $1 \times 10^6$ N417 cells/mouse in 100 µl of PBS into the intra-thoracic space. Three weeks after the tumor inoculation, the mice were injected with reporter or therapeutic gene-expressing plasmid DNA nanoparticles by systemic administration via tail vein with 25 µg plasmid DNA in 100 µl DOTAP/cholesterol. Two days after injection, all the mice were sacrificed, and the tumors, lungs, livers, spleens, kidneys and brains were collected and stored in frozen for further EGFP expression analyzing.
4. Human NSCLC subcutaneous tumor xenograft mouse model Procedures for NSCLC A549 and H1299 subcutaneous tumor inoculations in nu/nu mice were described previously (see Ji et al., 2002 and Uno et al., 2004, each of which is herein specifically incorporated by reference). Briefly, mice were irradiated at 350 Rd 137 Cs just one day before injection. $1 \times 10^7$ tumor cells suspended in 100 ml of PBS are subcutaneously injected into animals. About 10-14 days, solid tumors will start to form. For the in vivo imaging, animals will be injected intratumorily with DOTAP-cholesterol-complexed pLJ296/SSRT2A plasmid vectors (SSRT2A-Lipoplex) at a dose of 25 mg plasmid DNA:10 nmol nanoparticles/tumor each in 100 ml of D5W (5% Dextrose in water). PBS and empty vector are used as mock and negative controls, respectively. In vivo imaging will be performed 24-48 h after injection. For comparison, tumors are removed from animals 24-48 after the injection and fixed and sectioned for further pathologic, immunohistochemical analysis with HA antibody for the HA-SSRT2A fusion protein.
5. Human NSCLC experimental lung metastases mouse model. Briefly, mice were irradiated at 350 Rd 137Cs just one day before injection. nu/nu mice were inoculated with A549 cells ($1\text{-}2\times10^6$) in 200 µl PBS via tail vein injection. Pulmonary experimental metastases tumor colonies were formed 7-10 days after inoculation. For the in vivo imaging, animals were injected intravenously with DOTAP-cholesterol-complexed pLJ296/SSRT2A plasmid vectors (SSRT2A-Lipoplex) at a dose of 25 mg plasmid DNA:10 nmol liposome/tumor each in 100 ml of D5W (5% Dextrose in water). PBS and empty vector are used as mock and negative controls, respectively. In vivo imaging was performed 24-48 h after injection. To compare with in vivo imaging, lungs will be harvested 24-48 after the injection, and metastastic colonies on the surfaces of lung were stained with Indian ink. Tumor colonies on lung surfaces were counted under a dissecting microscope without knowledge of the treatment groups, and the lung tissues were sectioned for further pathologic, immunohistochemical analysis with HA antibody for the HA-SSRT2A fusion protein.
6. Human NSCLC H460 intra-thoracic tumor xenograft mouse model. Mice were irradiated at 350 Rd 137 Cs just one day before injection. nu/nu mice are inoculated with H460 cells ($5\times106$) in 100 µl PBS via intra-thoracic injection while animals are under anesthesia. Primary tumors inside thoracic space and metastatic tumors in bone, lymph node, or brain are formed 7-10 days after inoculation. For the in vivo imaging, animals were injected intravenously with DOTAP-cholesterol-complexed pLJ296/SSRT2A plasmid vectors (SSRT2A nanoparticle) at a dose of 25 mg plasmid DNA:10 nmol liposome/tumor each in 100 ml of D5W (5% Dextrose in water). PBS and empty vector were used as mock and negative controls, respectively. In vivo imaging was performed 24-48 h after injection. To compare with in vivo imaging, tumors were harvested 24-48 after the injection, and sectioned for further pathologic, immunohistochemical analysis with HA antibody for the HA-SSRT2A fusion protein. The whole animal cross-sectioning will be performed to confirm the in vivo imaging.
7. Analysis of in vivo gene expression. The expressions of EGFP in frozen sectioned normal tissues and tumors with different promoters was recorded with an equipped digital camera. Briefly, the frozen samples were cut to 5-10 µm sections, fixed in 4% paraformadehyde on ice for 10 minutes, rinsed in PBS. After air dry, tissue samples were covered with fluorescence enhancing cover medium (Vector Lab, Burlingame, Calif.) and a glass coverslip, and examined under a fluorescence microscope equipped with a digital camera and imaging analysis software.
8. Induction of apoptosis in hTMC- or CMV-FUS1-nanoparticle treated mice by in situ cell death analysis with TUNEL-reaction. Induction of apoptosis is detected in tumors in human lung cancer tumor-bearing mice treated by hTMC-FUS1-nanoparticle but not in normal lung and other tissues (FIG. 19). By comparison, no tumor selectivity is seen in mice treated by conventional CMV-FUS1-nanoparticles, as shown by flourescence images with an in situ apoptosis analysis with TUNEL staining in frozen mouse tissue sections (FIG. 19).

Example 2

A Novel Synthetic hTERT-Mini-CMV Chimera Promotor-Driven Tumor-Selective and High-Efficiency Expression of Transgene for Systemic Cancer Gene Therapy

One of the major obstacles to a successful cancer gene therapy is the lack of an effective systemic delivery system that can be specifically targeted to primary and metastatic tumors. The hTERT promoter has been cloned and showed to be capable of targeting transgene expression in tumors but not in the normal cells. However, the weak transcription-promoting strength of hTERT promoter, like most other intrinsic mammalian promoters, has hampered its direct use for cancer gene therapy. To circumvent these problems, a novel chimera hTERT-mini-CMV (hTMC) promoter has been developed that was engineered by optimally fusing essential hTERT regulatory sequence with minimal CMV promoter elements. Various human cancers and normal cells were transfected with various EGFP-constructs, in which EGFP expression is driven by either the original CMV and hTERT promoters or by the hTMC promoter in vitro. Expression of EGFP in the transfectants was visualized by a fluorescence imaging (FI) under a fluorescence microscope and the population of EGFP-positive cells and fluorescence intensity were quantified by FACS analysis. A high level of EGFP expression driven by the hTMC promoter was detected in all tumor cells but not in normal cells. While a similar tumor-selectivity of EGFP expression driven by hTERT promoter could be seen but the level of expression was several hundred-fold lower than that driven by hTMC promoter under the same transfection efficiency. The effectiveness of hTMC promoter was also evaluated in vivo by systemic injection of DOTAP:cholesterol-complexed hTMC-EGFP-nanoparticles into nude mice that bear intrathoracic human N417 lung tumor xenografts. Consistently, a high level of EGFP expression could be detected only in the tumor cells in animals treated with hTMC-EGFP but not in any other normal tissues. Furthermore, the above N417 tumor mice model was used to evaluate the therapeutic efficacy of systemic treatment with a novel hTMC-FUS1-nanoparticle by a non-invasive and quantitative MR imaging analysis. A significant inhibition (P<0.001) of tumor growth was detected in animals treated by hTMC-FUS1-nanoparticles in less than 2 weeks of treatment compared to those untreated or treated by hTMC-EGFP-nanoparticles, as demonstrated by MR imaging and volume analysis. Induction of apoptosis was also detected in tumor cells but not in surrounding normal lung or other normal tissues in mice treated by hTMC-FUS1-nanoparticles, as shown by an in situ cell death analysis with TUNEL staining in frozen tissue samples. These results clearly demonstrate the capability of using the hTMC promoter to achieve both the high tumor-specificity and high-efficiency therapeutic gene expression in vitro and in vivo and implicate the translational applications of using the systemic administration of therapeutic hTMC-nanoparticle for tumor-targeted molecular cancer therapy.

\* \* \*

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 4,797,368
U.S. Pat. No. 5,139,941
U.S. Pat. No. 5,925,565
U.S. Pat. No. 5,928,906
U.S. Pat. No. 5,935,819
Abdul-Ghani et al., *Mol. Ther.*, 2: 539-544, 2000.
Aksentijevich et al., *Hum. Gene Ther.*, 7(9):1111-1122, 1996.
Alam and Cook, *Anal. Biochem.*, 188:245-254, 1990.
Alberico et al., *Surg. Oncol. Clin. N. Am.*, 13(1):13-35, 2004.
Angel et al., *Mol. Cell. Biol.*, 7:2256, 1987.
Artemov et al., *Mag. Reson. Med.*, 49:403-408, 2003.
Atchison and Perry, *Cell*, 46:253, 1986.
Atchison and Perry, *Cell*, 48:121, 1987.
Banerji et al., *Cell*, 27(2 Pt 1):299-308, 1981.
Banerji et al., *Cell*, 33(3):729-740, 1983.
Beattie et al., *Curr Biol.*, 8(3):177-180, 1998.
Berkhout et al., *Cell*, 59:273-282, 1989.
Blackburn et al., *J. Lipid. Res.*, 32(12):1911-1918, 1991.
Blumberg et al., *Cell*, 104(1):9-19, 2001.
Bodine and Ley, *EMBO J.*, 6:2997, 1987.
Boshart et al., *Cell*, 41:521, 1985.
Bosze et al., *EMBO J*, 5(7):1615-1623, 1986.
Boussif et al., *Proc. Natl. Acad. Sci. USA*, 92(16):7297-7301, 1995.
Braddock et al., *Cell*, 58:269, 1989.
Bulla and Siddiqui, *J. Virol.*, 62:1437, 1986.
Caley et al., *J. Virology*, 71(4):3031-3038, 1997.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Celander and Haseltine, *J. Virology*, 61:269, 1987.
Celander et al., *J. Virology*, 62:1314, 1988.
Chandler et al., *Proc. Natl. Acad. Sci. USA*, 94(8):3596-601, 1997.
Chang et al., *Mol. Cell. Biol.*, 9:2153, 1989.
Chen and Okayama, *Mol. Cell Biol.*, 7(8):2745-2752, 1987.
Choi et al., *Cell*, 53:519, 1988.
Coffin, In: *Virology*, Fields et al. (Eds.), Raven Press, NY, 1437-1500, 1990.
Cohen et al., *J. Cell. Physiol.*, 5:75, 1987.
Costa et al., *Mol. Cell. Biol.*, 8:81, 1988.
Couch et al., *Am. Rev. Resp. Dis.*, 88:394-403, 1963.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
Davis et al., *Curr. Biol.*, 6:146-148, 1996.
De Villiers et al., *Nature*, 312(5991):242-246, 1984.
de Waal et al., *J. Exp. Med.*, 174:1209-1220, 1991.
Deschamps et al., *Science*, 230:1174-1177, 1985.
Dumoutier et al., *J. Immunol.*, 164(4):1814-1819, 2000.

Edbrooke et al., *Mol. Cell. Biol.*, 9:1908, 1989.
Edlund et al., *Science*, 230:912-916, 1985.
Ekmekciouglu et al., *Melanoma Res.*, 9(3):261-272, 1999.
Fechheimer, et al., *Proc Natl. Acad. Sci. USA*, 84:8463-8467, 1987.
Felgner et al., *Proc. Natl. Acad. Sci. USA*, 84(21):7413-7417, 1987.
Feng and Holland, *Nature*, 334:6178, 1988.
Feng et al., *Science*, 269(5228):1236-1241, 1995.
Firak and Subramanian, *Mol. Cell. Biol.*, 6:3667, 1986.
Foecking and Hofstetter, *Gene*, 45(1):101-105, 1986.
Fraley et al., *Bio/Technology*, 3:629-635, 1985.
Fujita et al., *Cell*, 49:357, 1987.
Gabizon et al., *Cancer Res.*, 50(19):6371-6378, 1990.
Gallagher et al., *Genes Immun.*, 1(7):442-450, 2000.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gilles et al., *Cell*, 33:717, 1983.
Glorioso et al., *Mol. Biotechnol.*, 4(1):87-99, 1995.
Gloss et al., *EMBO J.*, 6:3735, 1987.
Godbout et al., *Mol. Cell. Biol.*, 8:1169, 1988.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Graham and Van Der Eb, *Virology*, 52:456-467, 1973.
Greene et al., *Immunology Today*, 10:272, 1989.
Grosschedl and Baltimore, *Cell*, 41:885, 1985.
Gu et al., *Cancer Res.*, 60:5359-5364, 2000.
Gu et al., *Oncogene*, 21:4757-4764, 2002.
Gupta and Curtis, *J. Mat. Sci. Mat. Med.*, 15:493-496, 2004.
Harland and Weintraub, *J. Cell Biol.*, 101(3):1094-1099, 1985.
Harrington et al., *Gene Dev.*, 11:3109-3115, 1997.
Hauber and Cullen, *J. Virology*, 62:673, 1988.
Hen et al., *Nature*, 321:249, 1986.
Henson et al., *AJNR Am. J. Neuroradiol.*, 25(6):969-972, 2004.
Herr and Clarke, *Cell*, 45:461, 1986.
Hirochika et al., *J. Virol.*, 61:2599, 1987.
Hirsch et al., *Mol. Cell. Biol.*, 10: 1959, 1990.
Holbrook et al., *Virology*, 157:211, 1987.
Horlick and Benfield, *Mol. Cell. Biol.*, 9:2396, 1989.
Hwang et al., *Mol. Cell. Biol.*, 10:585, 1990.
Imbra and Karin, *Nature*, 323:555, 1986.
Imler et al., *Mol. Cell. Biol.*, 7:2558, 1987.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Ji et al., *Cancer Res.*, 62:2715-2720, 2002.
Jiang et al., *Oncogene*, 11(12):2477-2486, 1995.
Jiang et al., *Proc. Natl. Acad. Sci. USA*, 93(17):9160-9165, 1996.
Johnson et al., *Mol. Cell. Biol.*, 9:3393, 1989.
Kadesch and Berg, *Mol. Cell. Biol.*, 6:2593, 1986.
Karin et al., *Mol. Cell. Biol.*, 7:606, 1987.
Katinka et al., *Cell*, 20:393, 1980.
Kawamoto et al., *Mol. Cell. Biol.*, 8:267, 1988.
Kiledjian et al., *Mol. Cell. Biol.*, 8:145, 1988.
Kim et al., *Cell*, 87:343-355, 1996.
Klamut et al., *Mol. Cell. Biol.*, 10:193, 1990.
Knapp et al., *Atherosclerosis*, 152(1):217-227, 2000.
Koch et al., *Mol. Cell. Biol.*, 9:303, 1989.
Komata et al., *Cancer Res.*, 61(15):5796-5802, 2001.
Kotenko et al., *Proc. Natl. Acad. Sci. USA*, 97(4):1695-1700, 2000.
Kotin et al., *Proc. Natl. Acad. Sci. USA*, 87(6):2211-2215, 1990.
Kriegler and Botchan, In: *Eukaryotic Viral Vectors*, Gluzman (Ed.), Cold Spring Harbor: Cold Spring Harbor Laboratory, N.Y., 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kundra et al., *J. Nuc. Med.*, 43:406-412, 2002.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Laughlin et al., *J. Virol.*, 60(2):515-524, 1986.
Lebkowski et al., *Mol. Cell. Biol.*, 8(10):3988-3996, 1988.
Levinson et al., *Nature*, 295:79, 1982.
Li et al. *J. Biol. Chem.*, 266:6562-6570, 1990.
Lin et al., *Mol. Cell. Biol.*, 10:850, 1990.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
McCarty et al., *J. Virol.*, 65(6):2936-2945, 1991.
McLaughlin et al., *J. Virol.*, 62(6):1963-1973, 1988.
Meyerson et al., *Cell*, 90:785-795, 1997.
Miksicek et al., *Cell*, 46:203, 1986.
Moreau et al., *Nucl. Acids Res.*, 9:6047, 1981.
Muesing et al., *Cell*, 48:691, 1987.
Muzyczka, *Curr. Topics Microbiol. Immunol.*, 158:97-129, 1992.
Nakamura et al., *Science*, 277:955-959, 1997.
Nakayama et al., *Nature Genet.*, 18:65-68, 1998.
Ng et al., *Nuc. Acids Res.*, 17:601, 1989.
Nicolau and Sene, *Biochim. Biophys. Acta*, 721:185-190, 1982.
Ondek et al., *EMBO J.*, 6:1017, 1987.
Ornitz et al., *Mol. Cell. Biol.*, 7:3466, 1987.
PCT Appln. PCT/US99/05781
Pech et al., *Mol Cell. Biol.*, 9:396, 1989.
Pelletier and Sonenberg, *Nature*, 334(6180):320-325, 1988.
Perez-Stable and Constantini, *Mol. Cell. Biol.*, 10:1116, 1990.
Picard and Schaffner, *Nature*, 307:83, 1984.
Pinkert et al., *Genes and Dev.*, 1:268, 1987.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Redondo et al., *Science*, 247:1225, 1990.
Reisman and Rotter, *Mol. Cell. Biol.*, 9:3571, 1989.
Ripe et al., *Mol. Cell. Biol.*, 9:2224, 1989.
Rippe, et al., *Mol. Cell Biol.*, 10:689-695, 1990.
Rosen et al., *Cell*, 41:813, 1988.
Roux et al., *Proc. Natl. Acad. Sci. USA*, 86:9079-9083, 1989.
Sambrook et al., In: *Molecular Cloning*, Cold Spring Harbor Laboratory Press, Cold Spring Harbor, N.Y., 2001.
Samulski et al., *EMBO J.*, 10:3941-3950, 1991.
Samulski et al., *J. Virol.*, 63:3822-3828, 1989.
Satake et al., *J. Virology*, 62:970, 1988.
Schaffner et al., *J. Mol. Biol.*, 201:81, 1988.
Sharp and Marciniak, *Cell*, 59:229, 1989.
Shaul and Ben-Levy, *EMBO J.*, 6:1913, 1987.
Shay et al., *Leukemia*, 10(8):1255-1261, 1996.
Shelling and Smith, *Gene Therapy*, 1:165-169, 1994.
Sherman et al., *Mol. Cell. Biol.*, 9:50, 1989.
Sleigh and Lockett, *J. EMBO*, 4:3831, 1985.

Solodin et al., *Biochemistry*, 34(41):13537-13544, 1995.
Soo et al., *J. Cell. Biochem.*, 74(1):1-10, 1999.
Soo et al., *J. Cell. Biochem.*, 74(1):1-10, 1999.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Strunk and Schild, *Eur. Radiol.*, 14(6):1055-1062, 2004.
Sullivan and Peterlin, *Mol. Cell. Biol.*, 7:3315, 1987.
Swartzendruber and Lehman, *J. Cell. Physiology*, 85:179, 1975.
Takakura et al., *Cancer Res.*, 59(3):551-557, 1999.
Takebe et al., *Mol. Cell. Biol.*, 8:466, 1988.
Tearney et al., *J Urol.*, 157(5):1915-1919, 1997.
Templeton et al., *Nat. Biotechnol.*, 15:647-652, 1997.
Thierry et al., *Proc. Natl. Acad. Sci. USA*, 92(21):9742-9746, 1995.
Thiesen et al., *J. Virology*, 62:614, 1988.
Top et al., *J. Infect. Dis.*, 124:155-160, 1971.
Tratschin et al., *Mol. Cell. Biol.*, 4:2072-2081, 1984.
Treisman, *Cell*, 42:889, 1985.
Tronche et al., *Mol. Biol. Med.*, 7:173, 1990.
Trudel and Constantini, *Genes and Dev.*, 6:954, 1987.
Tsukamoto et al., *Nat. Genet.*, 9(3):243-248, 1995.
Tur-Kaspa et al., *Mol. Cell Biol.*, 6:716-718, 1986.
Tyndell et al., *Nuc. Acids. Res.*, 9:6231, 1981.
Umeoka et al., *Cancer Res.*, 64(17):6259-6265, 2004.
Uno et al., *Cancer Res.*, 64:2969-2976, 2004.
Vannice and Levinson, *J. Virology*, 62:1305, 1988.
Vasseur et al., *Proc Natl. Acad. Sci. USA*, 77:1068, 1980.
Wang and Calame, *Cell*, 47:241, 1986.
Weber et al., *Cell*, 36:983, 1984.
Weinberger et al. *Mol. Cell. Biol.*, 8:988, 1984.
Winoto and Baltimore, *Cell*, 59:649, 1989.
Wu and Wu, *Biochemistry*, 27: 887-892, 1988.
Wu and Wu, *J. Biol. Chem.*, 262:4429-4432, 1987.
Yang and Huang, *Gene Therapy*, 4 (9):950-960, 1997.
Yang et al., *Proc. Natl. Acad. Sci. USA*, 87:9568-9572, 1990.
Yutzey et al. *Mol. Cell. Biol.*, 9:1397, 1989.
Yutzey et al., *Mol. Cell. Biol.*, 9:1397-1405, 1989.
Zhang et al., *Zhonghua Jie He He Hu Xi Za Zhi.*, 23(6):358-360, 2000.
Zhao et al., *Bioconjug. Chem.*, 13:840-844, 2002.
Zhu et al., *Science*, 261(5118):209-211, 1993.

What is claimed is:

1. A nucleic acid comprising a promoter region, the promoter region being a mini-CMV promoter sequence operatively coupled to a tissue-selective promoter sequence
wherein operatively coupling the tissue-selective promoter sequence to the mini-CMV promoter sequence results in improved promoter function of the tissue-selective promoter sequence.

2. A nucleic acid comprising a promoter sequence consisting essentially of a mini-CMV promoter sequence operatively coupled to a tissue-selective promoter sequence
wherein operatively coupling the tissue-selective promoter sequence to the mini-CMV promoter sequence results in improved promoter function of the tissue-selective promoter sequence.

3. The nucleic acid of claim 1, wherein the mini-CMV sequence is SEQ ID NO:2.

4. A nucleic acid comprising SEQ ID NO:3.

5. The nucleic acid of claim 1, further defined as comprising a gene operatively coupled to the promoter.

6. The nucleic acid of claim 5, wherein the gene is a therapeutic gene or selectable marker.

7. The nucleic acid of claim 6, wherein the therapeutic gene is a tumor suppressor gene, a gene that induces apoptosis, a gene encoding an enzyme, a gene encoding an antibody, or a gene encoding a hormone.

8. The nucleic acid of claim 7, wherein the therapeutic gene is Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, FUS1, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPG-4, FHIT, PTEN, ING1, NOEY1, NOEY2, OVCA1, MADR2, 53BP2, IRF-1, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, Gene 26 (CACNA2D2), PL6, Beta*(BLU), LUCA-1 (HYAL1), LUCA-2 (HYAL2), 123F2 (RASSF1), 101F6, Gene 21(NPRL2), SEM A3 or MCC.

9. The nucleic acid of claim 8, wherein the therapeutic gene is FUS1.

10. The nucleic acid of claim 6, wherein the selectable marker is a drug selection marker, an enzyme, or an immunologic marker.

11. The nucleic acid of claim 1, further defined as being comprised in a plasmid.

12. The nucleic acid of claim 1, further defined as comprising a reporter sequence operatively coupled to the promoter sequence.

13. The nucleic acid of claim 12, wherein the reporter sequence is a polynucleotide encoding a somatostatin receptor amino acid sequence, a sodium iodide symporter amino acid sequence, a eukaryotic green fluorescence protein amino acid sequence, a red fluorescence protein amino acid sequence, a luciferase amino acid sequence, a β-galactosidase amino acid sequence, or a thymidine kinase amino acid sequence.

14. The nucleic acid of claim 13, wherein the somatostatin receptor amino acid sequence is a recombinant somatostatin receptor amino acid sequence, a somatostatin type 2 receptor amino acid sequence, or mutated somatostatin type 2 receptor amino acid sequence.

15. The nucleic acid of claim 14, wherein the somatostatin type 2 receptor amino acid sequence is a somatostatin receptor type 2A amino acid sequence.

16. The nucleic acid of claim 12, wherein the reporter sequence is operatively coupled with IRES and a second gene.

17. The nucleic acid of claim 16, wherein the second gene is operatively coupled to a second reporter.

18. The nucleic acid of claim 17, wherein the second reporter is a somatostatin receptor amino acid sequence, a sodium iodide symporter amino acid sequence, a luciferase amino acid sequence, a eukaryotic green fluorescence protein amino acid sequence, or a thymidine kinase amino acid sequence.

19. The nucleic acid of claim 16, wherein the second gene comprises a selectable marker or a therapeutic gene.

20. The nucleic acid of claim 19, wherein the second gene is a therapeutic gene that is a tumor suppressor gene, a gene that induces apoptosis, a gene encoding an enzyme, a gene encoding an antibody, or a gene encoding a hormone.

21. The nucleic acid of claim 19, wherein the tissue-selective promoter sequence is an hTERT promoter sequence, the second promoter sequence is a mini-CMV promoter sequence, and wherein the promoter is operatively coupled to a gene encoding FUS1, and wherein said nucleic acid is comprised in a plasmid.

22. A composition comprising:
   a) a nucleic acid comprising a promoter sequence consisting essentially of a mini-CMV promoter sequence operatively coupled to a tissue-selective promoter sequence; and
   b) a delivery vehicle for delivery of the promoter sequence into a cell in a subject.

23. The composition of claim 22, wherein said delivery vehicle is a nucleic acid, a plasmid, a viral vector, a prokaryotic cell, a eukaryotic cell, or a lipid.

24. The composition of claim 23, wherein said lipid is comprised in a liposome.

25. The composition of claim 24, wherein the liposome comprises a cationic lipid.

26. The composition of claim 25, wherein the cationic lipid is DOTAP:Chol.

27. The composition of claim 26, wherein the DOTAP:Chol further comprises nanoparticles.

28. The composition of claim 23, wherein said delivery vehicle is a viral vector that is an adenoviral vector, a retroviral vector, a vaccinia viral vector, an adeno-associated viral vector, or a poxviral vector.

29. The composition of claim 28, wherein said viral vector is an adenoviral vector.

30. The nucleic acid of claim 2, wherein the promoter consists of a mini-CMV promoter sequence operatively coupled to a tissue-selective promoter sequence.

31. The nucleic acid of claim 1, wherein the tissue-selective promoter sequence is an hTERT promoter sequence.

32. The nucleic acid of claim 31, wherein the hTERT promoter sequence is SEQ ID NO:1.

33. The nucleic acid of claim 2, wherein the tissue-selective promoter sequence is an hTERT promoter sequence.

34. The nucleic acid of claim 22, wherein the tissue-selective promoter sequence is an hTERT promoter sequence.

35. The nucleic acid of claim 30, wherein the tissue-selective promoter sequence is an hTERT promoter sequence.

* * * * *

UNITED STATES PATENT AND TRADEMARK OFFICE
CERTIFICATE OF CORRECTION

PATENT NO. : 8,658,778 B2  
APPLICATION NO. : 11/372246  
DATED : February 25, 2014  
INVENTOR(S) : Lin X. Ji, Bingliang Fang and Jack A. Roth It is certified that error appears in the above-identified patent and that said Letters Patent is hereby corrected as shown below:

On Title page, item (56) References Cited - Other Publications, delete the 10th reference on page 1 "Artemov et al., "MR Molecular Imaging of the Her-2/new Receptor in Breast Cancer Cells Using Targeted Iron Oxide Nanoparticles," Mag. Reson. Med., 49:403-408, 2003." and replace with --Artemov et al., "MR Molecular Imaging of the Her-2/neu Receptor in Breast Cancer Cells Using Targeted Iron Oxide Nanoparticles," Mag. Reson. Med., 49:403-408, 2003.-- therefor.

On Title page, item (56) References Cited - Other Publications, delete the 2nd reference on page 2 "Chan et al., "Role of prolyl hydroxylation in onconically stablixed hypoxia-inducible factor-1α," J. Biol. Chem., 277:40112-40117, 2002." and replace with --Chan et al., "Role of prolyl hydroxylation in oncogenically stabilized hypoxia-inducible factor-1α," J. Biol. Chem., 277:40112-40117, 2002.-- therefor.

In the Claims

Claim 8, column 55, line 64, delete "DPG-4," and replace with --DPC-4,-- therefor.

Claim 34, column 58, line 20, delete "nucleic acid" and replace with --composition-- therefor.

Signed and Sealed this  
Fourteenth Day of October, 2014

Michelle K. Lee  
*Deputy Director of the United States Patent and Trademark Office*

SEQUENCE LISTING

```
<160> NUMBER OF SEQ ID NOS: 3

<210> SEQ ID NO 1
<211> LENGTH: 463
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
ttggcccctc cctcgggtta ccccacagcc taggccgatt cgacctctct ccgctggggc      60
cctcgctggc gtccctgcac cctgggagcg cgagcggcgc gcgggcgggg aagcgcggcc    120
cagacccccg ggtccgcccg gagcagctgc gctgtcgggg ccaggccggg ctcccagtgg    180
attcgcgggc acagacgccc aggaccgcgc tccccacgtg gcggagggac tggggacccg    240 ggcaccgtc ctgccccttc accttccagc tccgcctcct ccgcgcggac cccgccccgt     300 cccgaccct cccgggtccc cggcccagcc ccctccggc cctcccagcc cctcccttc       360 ctttaccgcg gccccgccct ctcctcgcgg cgcgagtttc aggcagcgct gcgtcctgct    420
gcgcacgtgg gaagccctgg ccccggccac ccccgccaga tct                      463

<210> SEQ ID NO 2
<211> LENGTH: 117
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
gtaggcgtgt acggtgggag gcctatataa gcagagctcg tttagtgaac cgtcagatcg     60
cctggagacg ccatccacgc tgttttgacc tccatagaag acaccgggac cgatcca       117

<210> SEQ ID NO 3
<211> LENGTH: 585
<212> TYPE: DNA
<213> ORGANISM: Artificial Sequence
<220> FEATURE:
```

```
-continued

<223> OTHER INFORMATION: Description of Artificial Sequence:  Synthetic
      Primer

<400> SEQUENCE: 3
ttggccsctc cctcgggtta ccccacagcc taggccgatt cgacctctct ccgctggggc      60
cctcgctggc gtccctgcac cctgggagcg cgagcggcgc gcgggcgggg aagcgcggcc    120 cagaccccg gtccgcccg gagcagctgc gctgtcgggg ccaggccggg ctcccagtgg      180 attcgcggc acagacgccc aggaccgcgc tccccacgtg gcggagggac tggggacccg     240 ggcaccgtc ctgcccttc accttccagc tccgcctcct ccgcgcggac cccgccccgt      300
cccgacccct cccgggtccc cggcccagcc ccctccgggc cctcccagcc cctccccttc    360
ctttaccgcg gccccgccct ctcctcgcgg cgcgagtttc aggcagcgct gcgtcctgct    420
gcgcacgtgg gaagccctgg ccccggccac ccccgccaga tctgatctgt aggcgtgtac    480
ggtgggaggc ctatataagc agagctcgtt tagtgaaccg tcagatcgcc tggagacgcc    540
atccacgctg ttttgacctc catagaagac accgggaccg atcca                    585
```